(12) United States Patent
Takiguchi

(10) Patent No.: US 10,168,521 B2
(45) Date of Patent: Jan. 1, 2019

(54) STIMULATED EMISSION DEPLETION MICROSCOPE

(71) Applicant: HAMAMATSU PHOTONICS K.K., Hamamatsu-shi, Shizuoka (JP)

(72) Inventor: Yuu Takiguchi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 81 days.

(21) Appl. No.: 15/301,484

(22) PCT Filed: Mar. 19, 2015

(86) PCT No.: PCT/JP2015/058289
§ 371 (c)(1),
(2) Date: Oct. 3, 2016

(87) PCT Pub. No.: WO2015/151838
PCT Pub. Date: Oct. 8, 2015

(65) Prior Publication Data
US 2017/0031145 A1 Feb. 2, 2017

(30) Foreign Application Priority Data
Apr. 4, 2014 (JP) ................................ 2014-077642

(51) Int. Cl.
*G01N 21/64* (2006.01)
*G02B 21/00* (2006.01)
*G02B 26/06* (2006.01)

(52) U.S. Cl.
CPC ..... *G02B 21/0076* (2013.01); *G01N 21/6458* (2013.01); *G02B 21/0032* (2013.01);
(Continued)

(58) Field of Classification Search
CPC ............ G02B 21/0076; G02B 21/0032; G02B 21/0036; G01N 21/6458
See application file for complete search history.

(56) References Cited

U.S. PATENT DOCUMENTS

2006/0007535 A1* 1/2006 Gugel ................... G02B 21/16
359/387
2009/0046298 A1* 2/2009 Betzig ................ G01N 21/6445
356/521

(Continued)

FOREIGN PATENT DOCUMENTS

CN 103389573 11/2013
CN 103487421 1/2014

(Continued)

OTHER PUBLICATIONS

Watanabe et al., "Formation of a doughnut laser beam for super-resolving microscopy using a phase spatial light modulator," May 2004, Optical Engineering, vol. 43, No. 5, pp. 1136-1143.*

(Continued)

*Primary Examiner* — Kiho Kim
(74) *Attorney, Agent, or Firm* — Drinker Biddle & Reath LLP

(57) ABSTRACT

An STED microscope apparatus includes an STED light source for outputting STED light, an excitation light source for outputting excitation light, a phase modulation type SLM for presenting a phase pattern for shaping the STED light in an annular shape by phase modulation, an optical system for irradiating an observation object region with the excitation light and the STED light after phase modulation, a detector for detecting fluorescence generated from the observation object region, and a control unit for controlling the phase pattern. The control unit sets the phase pattern for controlling the inner diameter of the annular shape of the STED light after phase modulation.

11 Claims, 19 Drawing Sheets

(52) U.S. Cl.
CPC ..... *G02B 21/0036* (2013.01); *G02B 21/0056* (2013.01); *G02B 26/06* (2013.01)

(56) References Cited

U.S. PATENT DOCUMENTS

| | | | |
|---|---|---|---|
| 2011/0174986 A1 | 7/2011 | Kempe et al. | |
| 2012/0257197 A1* | 10/2012 | Feldkhun | G01N 21/4795 356/301 |
| 2013/0057869 A1* | 3/2013 | Cotte | G02B 21/365 356/457 |

FOREIGN PATENT DOCUMENTS

| | | |
|---|---|---|
| JP | 2012-504226 A | 2/2012 |
| JP | 2013-092687 A | 5/2013 |
| JP | 2013-092688 A | 5/2013 |
| WO | WO-2010/037486 A2 | 4/2010 |
| WO | WO-2013/118810 A1 | 8/2013 |

OTHER PUBLICATIONS

Mei et al., "Random sources generating ring-shaped beams," 2013, Optics Letters, vol. 38, No. 2, pp. 91-93.*
Dasgupta et al., "Optical orientation and ortation of trapped red blood cells with laguerre-Gaussian mode," 2011, Optics Express, vol. 19, No. 8, pp. 7680-7688.*
International Preliminary Report on Patentability dated Oct. 13, 2016 for PCT/JP2015/058289.
Travis J. Gould et al., "Adaptive optics enables 3D STED microscopy in aberrating specimens," Optics Express, 2012, pp. 20998-21009, vol. 20, No. 19.

* cited by examiner (a)

(b)

(a)

P₁₁

(b)

P₁₂

(c)

P₁₃

(d)

P₁₄

(a)

LS₂

(b)

LS₂

(c)

LS₂

(d)

LS₂

(a)

(b)

(c)

(a)

(b)

(c)

(a)

(b)

(c)

(a)

(b)

(a)

(b)

(a)

(b)

(c)

STIMULATED EMISSION DEPLETION MICROSCOPE

TECHNICAL FIELD

An aspect of the present invention relates to a stimulated emission depletion microscope apparatus.

BACKGROUND ART

Non Patent Document 1 discloses a technology that relates to a stimulated emission depletion (STED) microscope. In the STED microscope disclosed in this document, an annular STED beam is generated using a phase modulation type spatial light modulator.

CITATION LIST

Patent Literature

Patent Document 1: Japanese Patent Application Laid-Open Publication No. 2013-92687

Non Patent Literature

Non Patent Document 1: Travis J. Gould et al., "Adaptive optics enables 3D STED microscopy in aberrating specimens", OPTICS EXPRESS Vol. 20 No. 19, pp. 20998-21009 (2012)

SUMMARY OF INVENTION

Technical Problem

Presently, a so-called super-resolution microscope of acquiring an image by a resolution of an optical diffraction limit or less has been developed. While various methods are proposed as super-resolution technologies used in the super-resolution microscope, an STED microscope is exemplified as one of these. The STED microscope can locally generate fluorescence from an observation object by irradiating the observation object substantially simultaneously with laser light serving as excitation light for observation (hereinafter referred to as an excitation beam) and short pulse laser light for stimulated emission (hereinafter referred to as an STED beam).

A principle of the STED microscope will be described below. (a) in FIG. 18 and (b) in FIG. 18 are views showing a generation principle of fluorescence. As shown in (a) in FIG. 18, when an observation object is irradiated with excitation light LE having an excitation wavelength, electrons are excited from a ground state to an excited state (an arrow A1 in the figure). After that, the electrons transit from the excited state to the ground state for several microseconds (an arrow A2 in the figure), and at this time, fluorescence PL having a wavelength corresponding to an energy difference between the ground state and the excited state is generated.

On the other hand, in (b) in FIG. 18, the observation object is irradiated with STED light LS after a predetermined time difference from irradiation with the above-described excitation light LE. The electrons excited to the excited state by the excitation light LE are induced by the STED light LS to transit to the ground state (an arrow A3 in the figure). Here, since they transit with an energy corresponding to the wavelength of the STED light LS, the wavelength of the generated light LA is equal to the wavelength of the STED light LS. According to the above-described action, in a region which is irradiated with the STED light LS after irradiated with the excitation light LE, light LA having a different wavelength from the fluorescence PL is generated instead of the fluorescence PL. Further, as the predetermined time difference is on the nano-order, a time difference may be provided between a generation timing of the fluorescence PL and a generation timing of the light LA.

FIG. 19 includes views showing examples of shapes of (a) the excitation light LE, (b) the STED light LS, and (c) the fluorescence PL, respectively. In the STED microscope, as shown in (a) in FIG. 19, a certain observation object region is first irradiated with circular-shaped excitation light LE. After that, as shown in (b) in FIG. 19, the circular-shaped region is further irradiated with the annular-shaped STED light LS. Accordingly, since generation of the fluorescence PL is suppressed in the annular-shaped region, as shown in (c) in FIG. 19, the fluorescence PL can be generated from only an extremely small region near the center of the annular shape (a region surrounded by the annular shape), and the image can be acquired according to a resolution of a diffraction limit or less.

In the above-described STED microscope, the resolution is determined by a diameter $D_2$ of the fluorescence PL shown in (c) in FIG. 19. While the diameter $D_2$ is preferably small in order to improve the resolution, this may increase a time required for scanning the entire observation object region. Further, when the diameter $D_2$ is increased to shorten the time required for scanning the entire observation object region, the resolution may be reduced. For this reason, in the conventional STED microscope, only one of improvement of the resolution and reduction of the required time can be realized, and convenience may be insufficient.

The present invention has been made in view of the above problem, and an object of one aspect is to provide an STED microscope apparatus capable of improving user convenience related to resolution and required time.

Solution to Problem

In order to solve the above problem, an STED microscope apparatus according to one aspect of the present invention is an apparatus for irradiating an observation object with STED light and excitation light and detecting fluorescence, and the apparatus includes an STED light source for outputting STED light, an excitation light source for outputting excitation light, a phase modulation type first spatial light modulator for presenting a first phase pattern for shaping the STED light in an annular shape by phase modulation, an optical system for irradiating an observation object region with the excitation light and the STED light after phase modulation, a detector for detecting fluorescence generated from the observation object region, and a control unit for controlling the first phase pattern, and the control unit sets the first phase pattern for controlling an inner diameter of the annular shape of the STED light after phase modulation.

Further, an STED microscopy method according to one aspect of the present invention is a method of irradiating an observation object with STED light and excitation light and detecting fluorescence, and the method includes a step of outputting STED light by an STED light source (an STED light output step), a step of outputting excitation light by an excitation light source (an excitation light output step), a step of phase-modulating the STED light by a phase modulation type first spatial light modulator for presenting a first phase pattern for shaping the STED light in an annular shape (a modulation step, a first modulation step), a step of irradiating an observation object region with the excitation light and the STED light after phase modulation by an optical system (an irradiation step), a step of detecting fluorescence generated from the observation object region by a detector (a detection step), and a step of setting a first phase pattern for controlling an inner diameter of the annular shape of the STED light after phase modulation (a setting step).

In the above-described STED microscope apparatus and the STED microscopy method, the STED light output from the STED light source is shaped in an annular shape by phase modulation in the first spatial light modulator. The observation object region is irradiated with the annular STED light after the observation object region is irradiated with the excitation light. Accordingly, generation of the fluorescence is suppressed in the annular region, and the fluorescence is generated from only a region surrounded by the annular STED light. Therefore, according to the STED microscope apparatus and the STED microscopy method, an image can be acquired according to a resolution of a diffraction limit or less.

Further, in the STED microscope apparatus and the STED microscopy method, the inner diameter of the annular shape of the STED light after phase modulation can be changed by the control unit changing the phase pattern. Accordingly, the inner diameter of the annular shape can be reduced when improvement of the resolution is required, and the inner diameter of the annular shape can be increased when a time required for scanning the entire observation object region is decreased. In this way, according to the STED microscope apparatus and the STED microscopy method, user convenience related to the resolution and the required time can be improved.

Advantageous Effects of Invention

According to the STED microscope apparatus of one aspect of the present invention, user convenience related to resolution and required time can be improved.

DESCRIPTION OF EMBODIMENTS

Hereinafter, an embodiment of a stimulated emission depletion (STED) microscope apparatus according to the present invention will be described in detail with reference to the accompanying drawings. In addition, in the description of the drawings, the same elements will be denoted by the same reference symbols, and overlapping description will be omitted.

Figure 1:
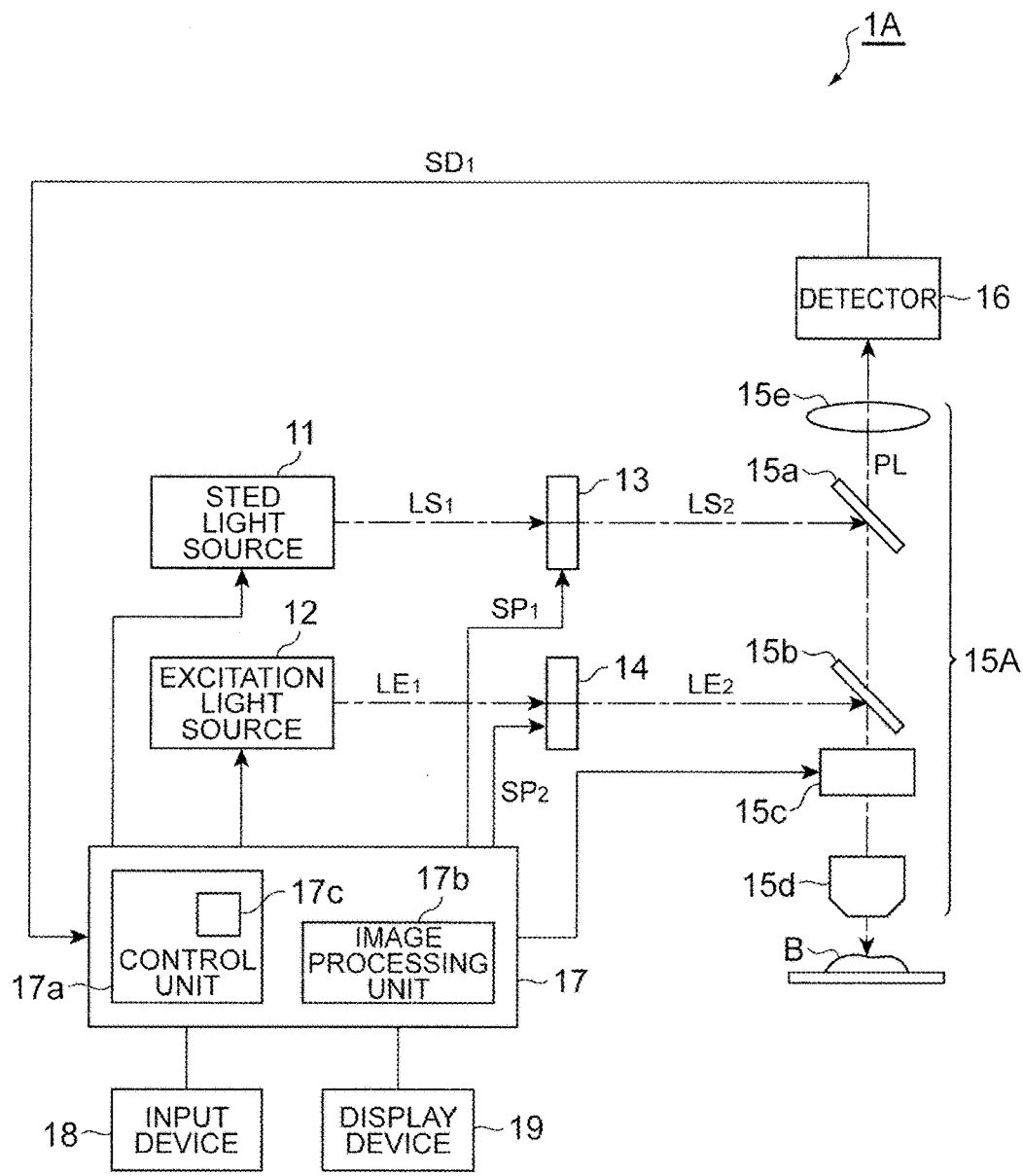
FIG. 1 is a block diagram showing a configuration of an STED microscope apparatus according to a first embodiment.

FIG. 1 is a block diagram showing a configuration of an STED microscope apparatus 1A according to a first embodiment of the present invention. The STED microscope apparatus 1A is an apparatus for acquiring a fluorescence image of an observation object B, for example, a cell sample. As shown in FIG. 1, the STED microscope apparatus 1A of the embodiment includes an STED light source 11, an excitation light source 12, spatial light modulators (SLM) 13 and 14, an optical system 15A, a detector 16, and an arithmetic control device 17.

The STED light source 11 is a light source for generating and outputting STED light $LS_1$. The STED light source 11 is, for example, a pulse light source for outputting light having high coherency such as laser light. For example, a lamp-based light source, a laser light source such as a laser diode, an LED, or the like, may be used as the STED light source 11. A wavelength of the STED light $LS_1$ is an arbitrary wavelength included in a wavelength band of fluorescence PL without overlapping with a peak wavelength of the fluorescence PL generated in the observation object B. Further, the STED light source 11 may not be a pulse light source, or, for example, may be constituted by a combination of a light source for outputting continuous light (CW light) and an optical shutter or an AOM (Acousto-Optic Modulator) for pulse modulation.

The excitation light source 12 is a light source for generating and outputting excitation light $LE_1$. The excitation light source 12 is, for example, a pulse light source for outputting light having high coherency such as laser light. For example, a laser light source such as a laser diode, an LED, or the like, may be used as the excitation light source 12. A wavelength of the excitation light $LE_1$ is a wavelength including an excitation wavelength of a fluorescent material which is contained in the observation object B described later. Further, the excitation light source 12 may not be a pulse light source, or, for example, may be constituted by a combination of a light source for outputting continuous light (CW light) and an optical shutter or an AOM for pulse modulation.

The SLM 13 is a phase modulation type SLM, and modulates a phase of input light in each part of a two-dimensional modulation surface and outputs the light after phase modulation. The SLM 13 is a first spatial light modulator of the embodiment. The SLM 13 is optically coupled to the STED light source 11. The SLM 13 receives the STED light $LS_1$ from the STED light source 11 and outputs STED light $LS_2$ after modulation. The SLM 13 controls condensing irradiation conditions such as a condensing position, a condensing intensity, a condensing shape, and so on, of the STED light $LS_2$ by presenting a phase pattern (kinoform) obtained by numerical calculation on the modulation surface.

Figure 2:
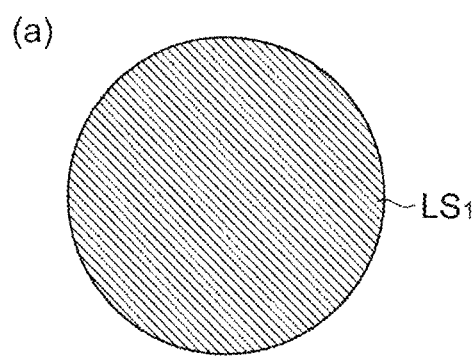
FIG. 2 includes (a) a view showing a cross-sectional shape perpendicular to an optical axis of STED light input into an SLM, and (b) a view showing a cross-sectional shape perpendicular to the optical axis of the STED light output from the SLM.
Figure 2:
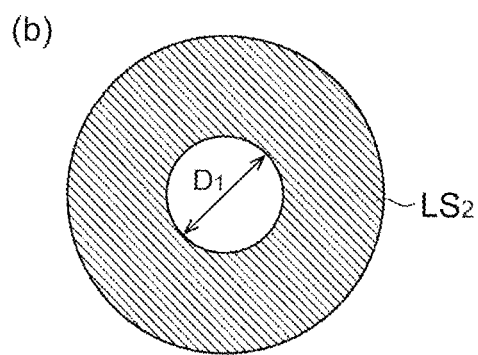

(a) in FIG. 2 is a view showing a cross-sectional shape perpendicular to an optical axis of the STED light $LS_1$ input into the SLM 13. Further, (b) in FIG. 2 is a view showing a cross-sectional shape perpendicular to an optical axis of the STED light $LS_2$ output from the SLM 13. In the embodiment, the STED light $LS_1$ having a circular shape as shown in (a) in FIG. 2 is input into the SLM 13, and in the SLM 13, an STED light shaping phase pattern (a first phase pattern) for shaping the STED light $LS_2$ into an annular shape having an inner diameter $D_1$ as shown in (b) in FIG. 2 by phase modulation is presented. The STED light shaping phase pattern is controlled by a pattern signal $SP_1$ sent from a control unit 17a of the arithmetic control device 17.

Here, the SLM 13 may be any one of a reflection type and a transmission type. Further, for example, a refractive index changing material type SLM is appropriately used as the SLM 13. For example, an LCOS (Liquid Crystal on Silicon) type SLM, an LCD (Liquid Crystal Display), an electric address type liquid crystal element, an optical address type liquid crystal element, a deformable mirror type SLM (a Segment Mirror type SLM, a Continuous Deformable Mirror type SLM), and so on, may be used as the SLM of the refractive index changing material type or the like.

Figure 19:
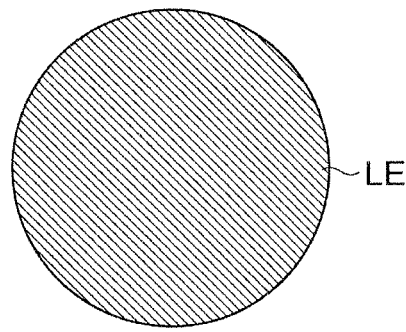
FIG. 19 includes views showing examples of shapes of (a) excitation light, (b) STED light, and (c) fluorescence, respectively.
Figure 19:
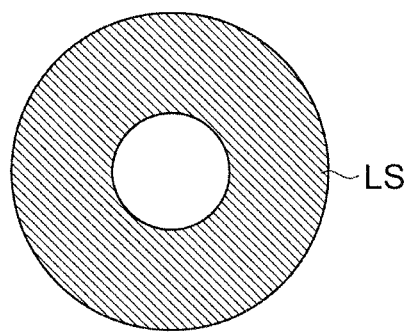
Figure 19:
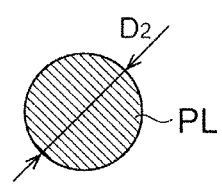

Returning to FIG. 1. The SLM 14 is a second spatial light modulator of the embodiment. The SLM 14 is optically coupled to the excitation light source 12. The SLM 14 receives the excitation light $LE_1$ from the excitation light source 12 and outputs excitation light $LE_2$ after modulation. The SLM 14 controls condensing irradiation conditions such as a condensing position, a condensing intensity, a condensing shape, and so on, of the excitation light $LE_2$ by presenting a phase pattern (kinoform) obtained by numerical calculation on the modulation surface. In the embodiment, in the SLM 14, an excitation light shaping phase pattern (a second phase pattern) for shaping the excitation light $LE_2$ in a circular shape (see (a) in FIG. 19) by phase modulation is presented. The excitation light shaping phase pattern is controlled by a pattern signal $SP_2$ sent from the control unit 17a.

Here, the SLM 14 may be a phase modulation type, or may be an intensity modulation (amplitude modulation) type. The same SLMs described above for the SLM 13 can be used as the phase modulation type SLM. Further, the SLM 14 may be any one of a reflection type and a transmission type. Further, instead of the SLM 14, a DOE (Diffractive Optical Element) may be installed. In the following description, the case in which the SLM 14 is the phase modulation type will be mainly described.

The optical system 15A is provided for irradiating an observation object region of the observation object B with the excitation light $LE_2$ and the STED light $LS_2$. The optical system 15A has an objective lens 15d optically coupled at least to the SLM 13 and the excitation light source 12. Further, in the STED microscope apparatus 1A, the optical system 15A has dichroic mirrors 15a and 15b, an optical scanner 15c, the objective lens 15d, and an imaging optical system 15e.

The dichroic mirror 15a reflects light of a wavelength band including a wavelength of the STED light $LS_2$ and transmits light of a wavelength band including a wavelength of the fluorescence PL generated in the observation object B. The dichroic mirror 15a is disposed on an optical axis that couples the objective lens 15d and the imaging optical system 15e. The dichroic mirror 15a receives the STED light $LS_2$ from the SLM 13 and reflects the STED light $LS_2$ toward the observation object B. Further, the dichroic mirror 15a transmits the fluorescence PL from the observation object B.

The dichroic mirror 15b reflects light of a wavelength band including a wavelength of the excitation light $LE_2$ and transmits light of a wavelength band including wavelengths of the STED light $LS_2$ and the fluorescence PL generated in the observation object B. The dichroic mirror 15b is disposed on an optical axis that couples the objective lens 15d and the dichroic mirror 15a. The dichroic mirror 15b receives the excitation light $LE_2$ from the SLM 14 and reflects the excitation light $LE_2$ toward the observation object B. Further, the dichroic mirror 15b transmits the STED light $LS_2$ from the dichroic mirror 15a and the fluorescence PL from the observation object B.

The optical scanner 15c is a device for scanning condensing positions of the STED light $LS_2$ and the excitation light $LE_2$ on the observation object B. The optical scanner 15c is optically coupled to the SLM 13, the excitation light source 12 and the objective lens 15d. The optical scanner 15c is disposed on an optical axis that couples the objective lens 15d and the dichroic mirror 15b. For example, a galvano, a resonant, a polygon mirror, a MEMS (Micro Electro Mechanical System) mirror, an acousto-optic element (an AOM or an AOD (Acousto-Optic Deflector)), or the like, is appropriately used as the optical scanner 15c.

The objective lens 15d is optically coupled to the SLM 13 and the excitation light source 12. The objective lens 15d is disposed to face the observation object B, for example, over the observation object, and allows the STED light $LS_2$ and the excitation light $LE_2$ to irradiate the observation object B while condensing the light. Here, the optical axes of the STED light $LS_2$ and the excitation light $LE_2$ are controlled by the SLMs 13 and 14 to coincide with each other. Further, the objective lens 15d collimates the fluorescence PL generated in the observation object B by irradiation with the excitation light $LE_2$.

The imaging optical system 15e is optically coupled to the objective lens 15d. The imaging optical system 15e is disposed on an optical axis between the dichroic mirror 15a and the detector 16. The imaging optical system 15e receives the fluorescence PL collimated by the objective lens 15d and passing through the dichroic mirrors 15a and 15b, and images the fluorescence PL on a detection surface of the detector 16.

The detector 16 detects light intensity of the fluorescence PL imaged by the imaging optical system 15e. For example, an optical sensor for detecting light intensity of one point such as a photomultiplier tube, a photodiode, or an avalanche photodiode, an area image sensor such as a CCD image sensor or a CMOS image sensor, a one-dimensional detector such as a line sensor, or a multi-anode photomultiplier tube is appropriately used as the detector 16. The detector 16 is optically coupled to the optical scanner 15c, and detects the fluorescence PL descanned by the optical scanner 15c and generated in the observation object B.

The detector 16 provides a light intensity signal $SD_1$ showing light intensity of the fluorescence PL to the arithmetic control device 17. In particular, when the multi-anode photomultiplier tube or an area image sensor is used, as in a fourth modification example to be described later, according to the configuration of generating a plurality of points by the SLM 13 and the SLM 14, fixed multi-point fluorescence PL in which the influence of scan is decreased can be detected by the detector 16, and a scan time can be reduced. Further, when the multi-anode photomultiplier tube is used, a configuration capable of adjusting a gain at each of the detection units is preferable.

The arithmetic control device 17 is constituted by, for example, a computer having a CPU and a memory. The arithmetic control device 17 includes the control unit 17a and an image processing unit 17b. The control unit 17a is electrically coupled to the SLM 13 and the SLM 14. The control unit 17a controls a first phase pattern presented in the SLM 13 and a second phase pattern presented in the SLM 14. That is, the control unit 17a determines an STED light shaping phase pattern presented in the SLM 13 based on a wavelength of the STED light $LS_1$, and a desired inner diameter and outer diameter of an annular shape of the STED light $LS_2$. Further, the control unit 17a determines an excitation light shaping phase pattern presented in the SLM 14 based on a wavelength of the excitation light $LE_1$, and a desired diameter of a circular shape of the excitation light $LE_2$.

Here, since the STED light $LS_1$ and the excitation light $LE_1$ have different wavelengths, the phase patterns are designed according to the respective wavelengths. Specifically, the STED light shaping phase pattern presented in the SLM 13 is designed based on the wavelength of the STED light $LS_1$, and the excitation light shaping phase pattern presented in the SLM 14 is designed based on the wavelength of the excitation light $LE_1$.

More specifically, the control unit 17a presents a sum $\phi_{SLM}=\phi_{kinoform}+\phi_{pat}$ of a phase pattern $\phi_{kinoform}$ of a kinoform designed to provide a phase distribution of condensing the STED light $LS_2$ at a predetermined position and a condensing control pattern $\phi_{pat}$ for shaping the STED light $LS_2$ in an annular shape on the SLM 13 as the STED light shaping phase pattern. Similarly, the control unit 17a presents a sum $\phi_{SLM}=\phi_{kinoform}+\phi_{pat}$ of a phase pattern $\phi_{kinoform}$ of a kinoform designed to provide a phase distribution of condensing the excitation light $LE_2$ at a predetermined position and a condensing control pattern $\phi_{pat}$ for shaping the excitation light $LE_2$ in a circular shape on the SLM 14 as the excitation light shaping phase pattern. Further, provided that a phase of light input into a phase type SLM is $\phi_{in}$ and a phase value provided in the phase type SLM is $\phi_{SLM}$, a phase $\phi_{out}$ of the output modulated light becomes $\phi_{out}=\phi_{SLM}+\phi_{in}$.

Further, in the STED microscope, it is necessary to irradiate the observation object B with the STED light $LS_2$ with a predetermined time difference from irradiation with the excitation light $LE_2$. For this reason, the control unit 17a controls light emission timings of the STED light source 11 and the excitation light source 12 such that the STED light source 11 perform irradiation with the STED light $LS_1$ having a pulse shape after lapse of the predetermined time from irradiation with the excitation light $LE_1$ having a pulse shape by the excitation light source 12. Further, the control unit 17a scans the condensing positions of the excitation light $LE_2$ and the STED light $LS_2$ on the observation object B by controlling the optical scanner 15c.

The image processing unit 17b inputs the light intensity signal $SD_1$ from the detector 16. The image processing unit 17b generates a fluorescence image based on light intensity of the fluorescence PL detected by the detector 16 and a condensing position by the optical scanner 15c. The fluorescence image generated by the image processing unit 17b is displayed on the display device 19. The display device 19 is electrically coupled to the image processing unit 17b.

Here, in the embodiment, the inner diameter $D_1$ (see (b) in FIG. 2) of the annular shape of the STED light $LS_2$ can be set or changed by the control unit 17a setting or changing the STED light shaping phase pattern presented in the SLM 13. This point will be described below.

Figure 3:
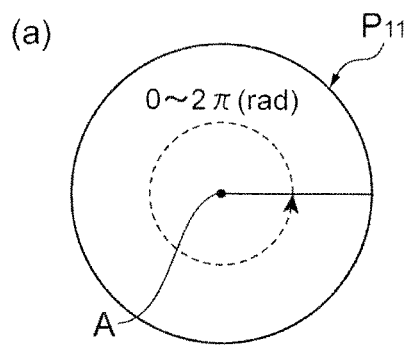
FIG. 3 includes (a)-(d) views conceptually showing patterns for shaping STED light in an annular shape included in an STED light shaping phase pattern presented in the SLM.
Figure 3:
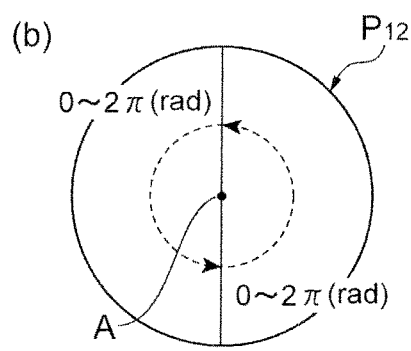
Figure 3:
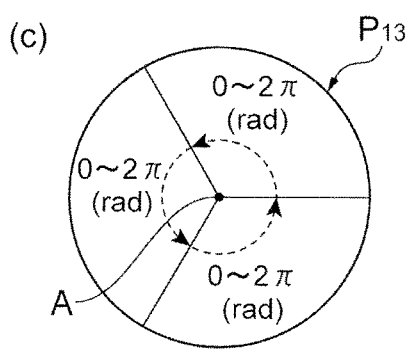
Figure 3:
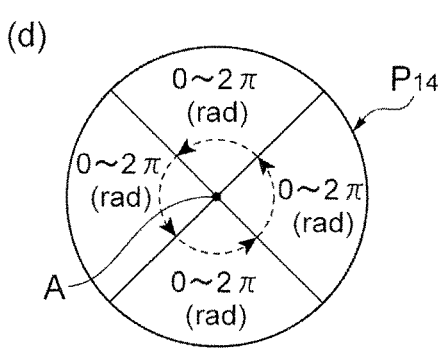

(a) in FIG. 3 to (d) in FIG. 3 are views conceptually showing patterns $P_{11}$ to $P_{14}$ for shaping the STED light $LS_2$ in an annular shape, which are included in the STED light shaping phase pattern presented in the SLM 13. Further, (a) in FIG. 4 to (d) in FIG. 4 are views showing phase values in pixels of the patterns $P_{11}$ to $P_{14}$ shown in (a) in FIG. 3 to (d) in FIG. 3, respectively, according to a density of color, and the phase value approaches 0 (rad) as the density of color is decreased, and the phase value approaches $2\pi$ (rad) as the density of color is increased.

Figure 4:
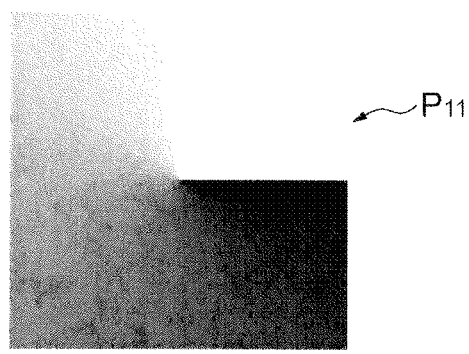
FIG. 4 includes (a)-(d) views showing phase values in pixels of the patterns shown in FIG. 3 according to a density of color.
Figure 4:
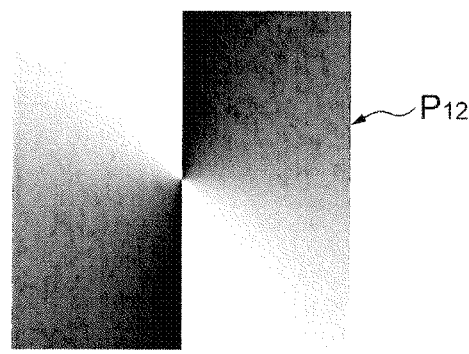
Figure 4:
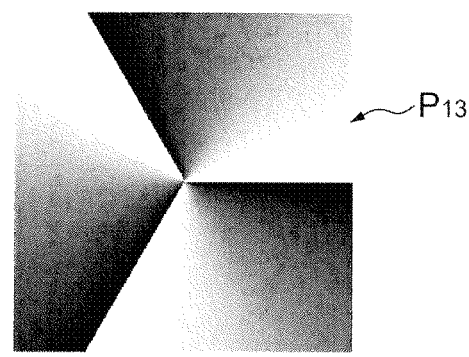
Figure 4:
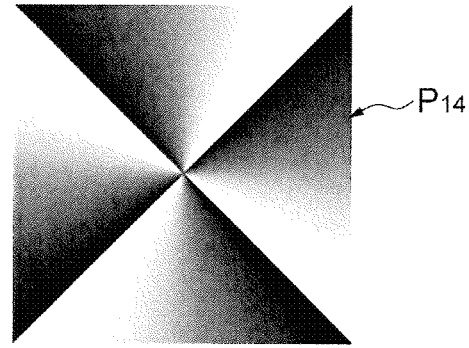

As shown in FIG. 3 and FIG. 4, these patterns $P_{11}$ to $P_{14}$ are patterns of repeating an increase of the phase from 0 (rad) to $2\pi$ (rad) spirally around a certain point A n times (n is an integer of 1 or more). (a) in FIG. 3 and (a) in FIG. 4 show the case of n=1, (b) in FIG. 3 and (b) in FIG. 4 show the case of n=2, (c) in FIG. 3 and (c) in FIG. 4 show the case of n=3, and (d) in FIG. 3 and (d) in FIG. 4 show the case of n=4.

Here, the patterns $P_{11}$ to $P_{14}$ are phase patterns of a so-called Laguerre-Gaussian (LG) beam. Such patterns $P_{11}$ to $P_{14}$ can also be expressed using Laguerre polynomials. Further, a gradation width in the STED light shaping phase pattern from 0 (rad) to $2\pi$ (rad) is set according to the wavelength of the STED light $LS_1$.

Figure 5:
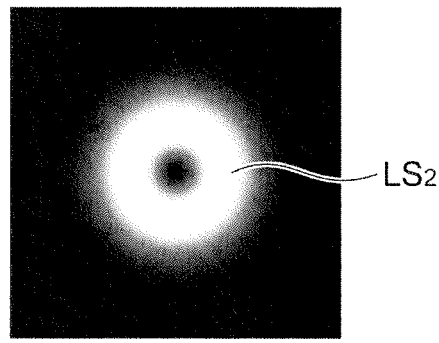
FIG. 5 includes (a)-(d) views showing shapes of the STED light obtained by presenting the patterns shown in FIG. 3 in the SLM.
Figure 5:
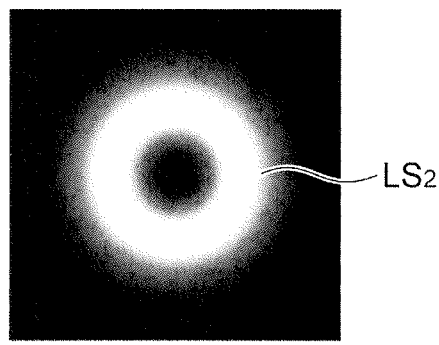
Figure 5:
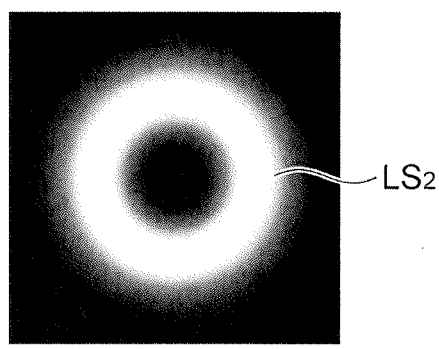
Figure 5:
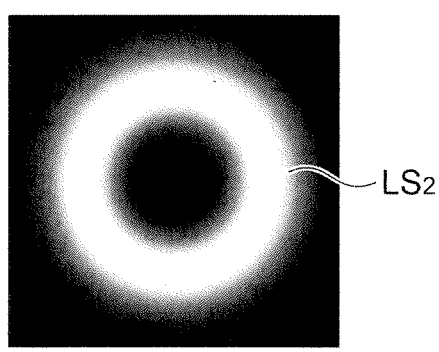

(a) in FIG. 5 to (d) in FIG. 5 are views showing shapes of the STED light $LS_2$ obtained by the SLM 13 presenting the above-described patterns $P_{11}$ to $P_{14}$. Further, in (a) in FIG. 5 to (d) in FIG. 5, the light intensity is shown by the density of color, where the density is decreased as the light intensity increases and the density is increased as the light intensity decreases. Referring to (a) in FIG. 5 to (d) in FIG. 5, as the number of repetitions n increases, the inner diameter of the annular shape of the STED light $LS_2$ increases. That is, the inner diameter $D_1$ of the annular shape shown in (b) in FIG. 2 can be controlled by the control unit 17a setting or changing the number of repetitions n.

The control unit 17a may have, for example, a storage unit 17c (see FIG. 1) for previously storing a plurality of patterns of the numbers of repetitions corresponding to the plurality of inner diameters $D_1$ of the annular shape. In this case, the control unit 17a selects a pattern corresponding to the inner diameter $D_1$ according to the desired inner diameter $D_1$ input from an input device 18 (an input unit, see FIG. 1) electrically coupled to the control unit 17a, and superimposes the pattern on the STED light shaping phase pattern. Alternatively, the control unit 17a may calculate the number of repetitions n that can realize the inner diameter $D_1$ according to the desired inner diameter $D_1$ input from the input device 18 electrically coupled to the control unit 17a, and superimpose the pattern based on the number of repetitions n on the STED light shaping phase pattern. Further, the storage unit 17c may be constituted by an external device electrically coupled to the arithmetic control device 17.

Figure 6:
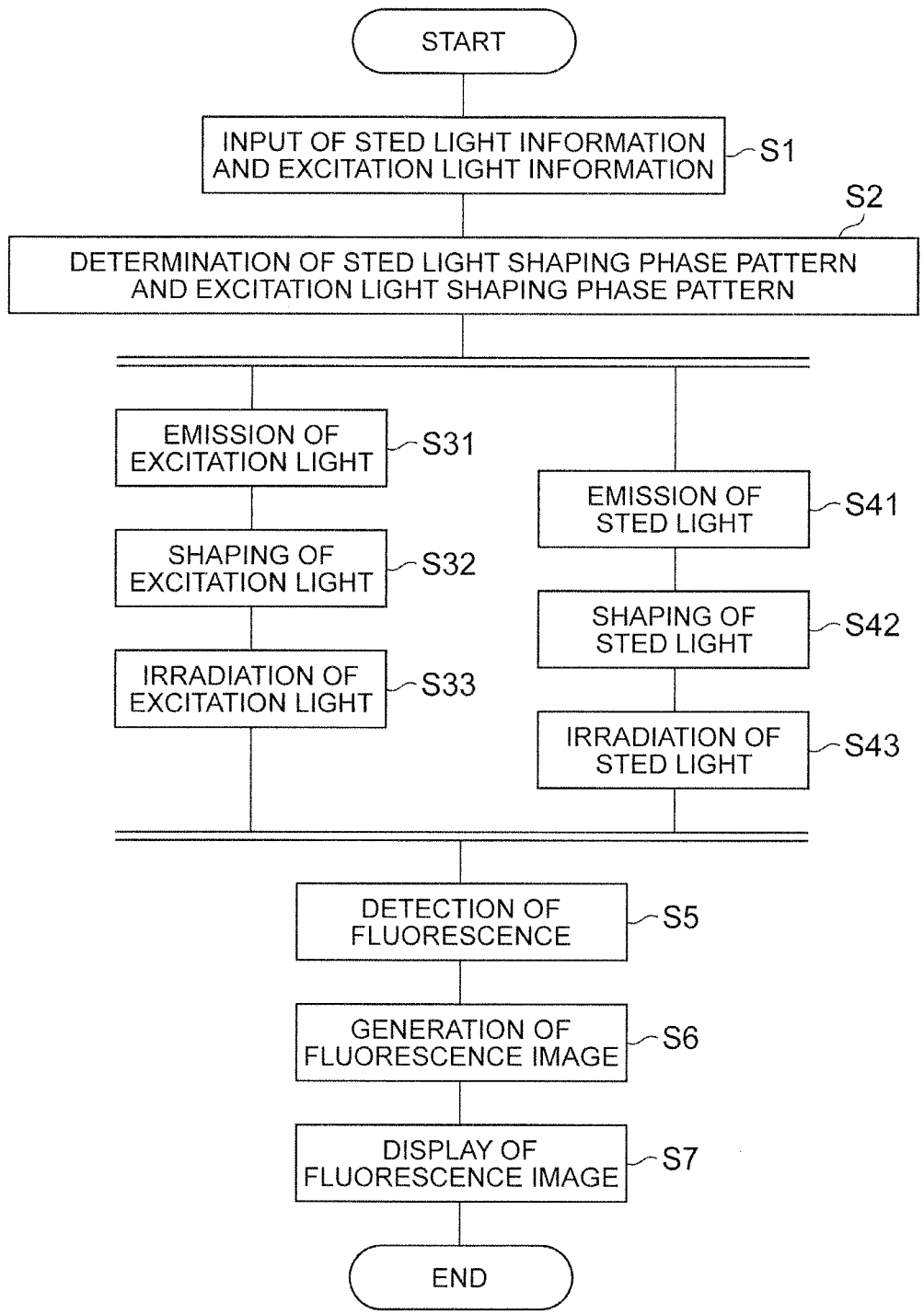
FIG. 6 is a flowchart showing an operation of the STED microscope apparatus.

An operation of the STED microscope apparatus 1A of the embodiment as described above will be described. FIG. 6 is a flowchart showing an operation of the STED microscope apparatus 1A. As shown in FIG. 6, first, information related to the STED light $LS_1$ and the excitation light $LE_1$ is input into the arithmetic control device 17 via the input device 18 (step S1). Next, the control unit 17a of the arithmetic control device 17 determines the STED light shaping phase pattern and the excitation light shaping phase pattern (step S2: setting step).

Then, the excitation light source 12 outputs the excitation light $LE_1$ according to an instruction from the control unit 17a (step S31: excitation light output step). After a delay of a predetermined time from the output of the excitation light $LE_1$, the STED light source 11 outputs the STED light $LS_1$ according to an instruction from the control unit 17a (step S41: STED light output step). The excitation light $LE_1$ is shaped in a circular shape by the SLM 14 (step S32: second modulation step), and the STED light $LS_1$ is shaped in an annular shape by the SLM 13 (step S42: modulation step, first modulation step).

The observation object region of the observation object B is irradiated with excitation light $LE_2$ after shaping via the dichroic mirror 15b, the optical scanner 15c, and the objective lens 15d (step S33). After that, after the predetermined time, the observation object region of the observation object B is further irradiated with the STED light $LS_2$ after shaping via the dichroic mirror 15a, the optical scanner 15c, and the objective lens 15d (step S43: irradiation step). Accordingly, in the annular region, generation of the fluorescence PL is suppressed, and the fluorescence PL is generated only from the region surrounded in the annular shape (see (c) in FIG. 19). Next, the light intensity of the fluorescence PL is detected by the detector 16 (step S5: detection step). The light intensity signal $SD_1$ related to the light intensity of the fluorescence PL is sent to the arithmetic control device 17 from the detector 16.

After completion of step S5, the condensing position of the STED light $LS_2$ and the excitation light $LE_2$ on the observation object B is moved by the optical scanner 15c. Then, steps S2 to S5 are performed again. In this way, by alternately repeating movement of the condensing position and steps S2 to S5, the intensities of the fluorescence PL are detected in a wide region of the observation object B. Next, the fluorescence image is generated in the image processing unit 17b of the arithmetic control device 17 (step S6). The fluorescence image is displayed on the display device 19 (step S7).

Further, in order to acquire a three-dimensional fluorescence image, after steps S1 to S6, a distance between the objective lens 15d and the observation object B is changed, and steps S1 to S6 may be performed again. Planar tomographic images are accumulated by repeating the above-described operation a plurality of times. After that, the image processing unit 17b may perform a three-dimensional image reconstruction processing based on the accumulated data. Further, an image group in which depths are continuously changed may be acquired by measuring a plurality of image acquisitions using a counter or the like and repeating an operation of moving the observation object B in an optical axis direction and changing the observation depth a plurality of times, and a three-dimensional image may be reconstructed through interpolation (linear interpolation, spline, or the like) between the images.

Figure 7:
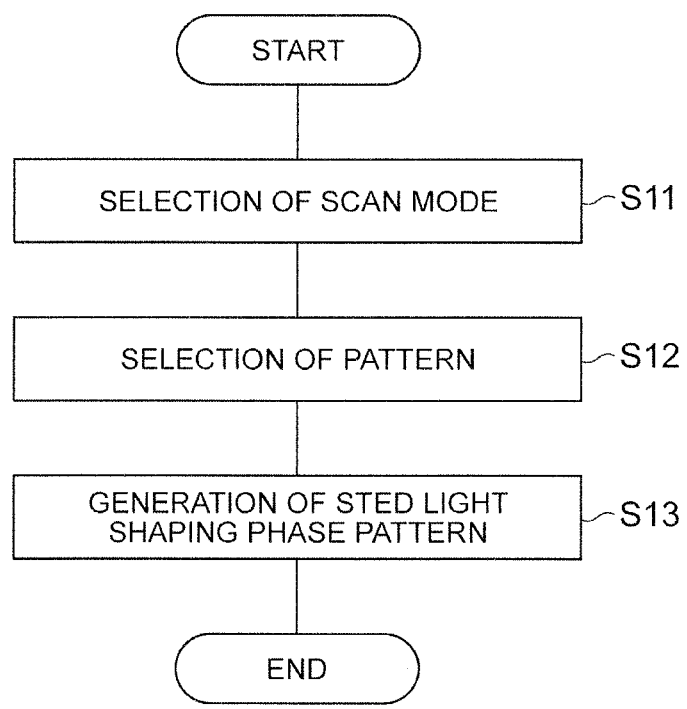
FIG. 7 is a flowchart showing processing of a control unit.

Further, the control unit 17a may previously store the plurality of patterns $P_{11}$ to $P_{14}$ corresponding to the plurality of inner diameters $D_1$ of the annular shape, and select an appropriate pattern from these patterns $P_{11}$ to $P_{14}$ according to the input from the input device 18. FIG. 7 is a flowchart showing processing of the control unit 17a. As shown in FIG. 7, first, a desired operation mode is selected by a user from a plurality of operation modes (scan modes) according to a plurality of scan times or a plurality of resolutions (step S11). Next, the control unit 17a selects a pattern corresponding to the selected operation mode from the patterns $P_{11}$ to $P_{14}$ (step S12). Next, the control unit 17a generates the STED light shaping phase pattern including the selected pattern, and presents the STED light shaping phase pattern in the SLM 13 (step S13).

Figure 8:
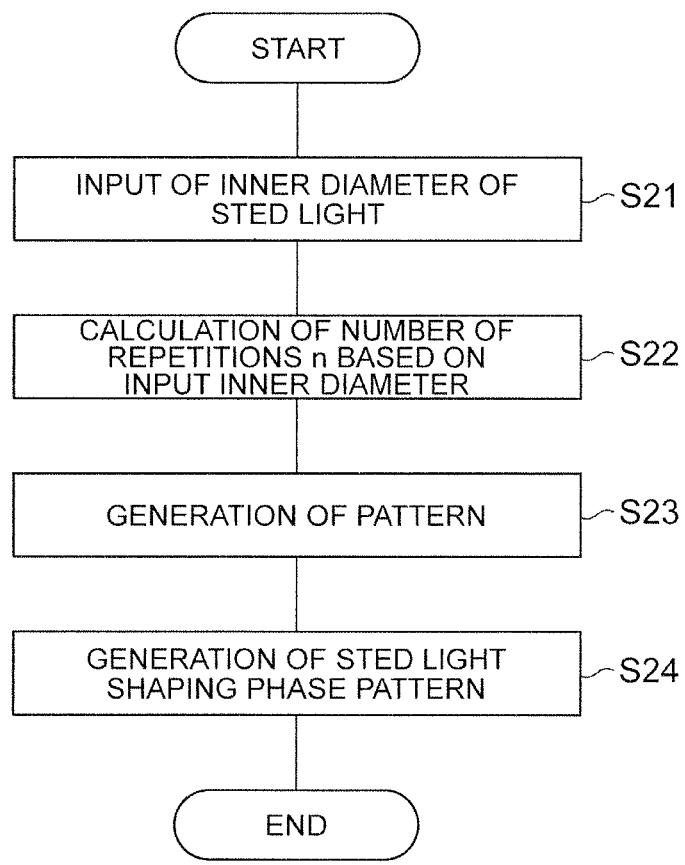
FIG. 8 is a flowchart showing processing of the control unit.

Furthermore, the control unit 17a may generate the STED light shaping phase pattern through the following processing. FIG. 8 is a flowchart showing processing of the control unit 17a. As shown in FIG. 8, first, the desired inner diameter $D_1$ is input by a user (step S21). Next, the control unit 17a calculates the number of repetitions n with which the inner diameter $D_1$ can be realized according to the desired inner diameter $D_1$ (step S22). Then, the control unit 17a generates the pattern based on the calculated number of repetitions n (step S23), generates the STED light shaping phase pattern including the pattern, and presents the STED light shaping phase pattern in the SLM 13 (step S24).

An effect obtained by the STED microscope apparatus 1A of the embodiment as described above will be described. In the STED microscope apparatus 1A, the STED light $LS_1$ output from the STED light source 11 is shaped in an annular shape by phase modulation in the SLM 13. The observation object region is further irradiated with the annular STED light $LS_2$ after the observation object region is irradiated with the excitation light $LE_2$. Accordingly, in the annular region, generation of the fluorescence PL is suppressed and the fluorescence PL is generated from only the region surrounded by the annular STED light $LS_2$. Therefore, according to the STED microscope apparatus 1A of the embodiment, an image with the resolution of a diffraction limit or less can be acquired.

Figure 9:
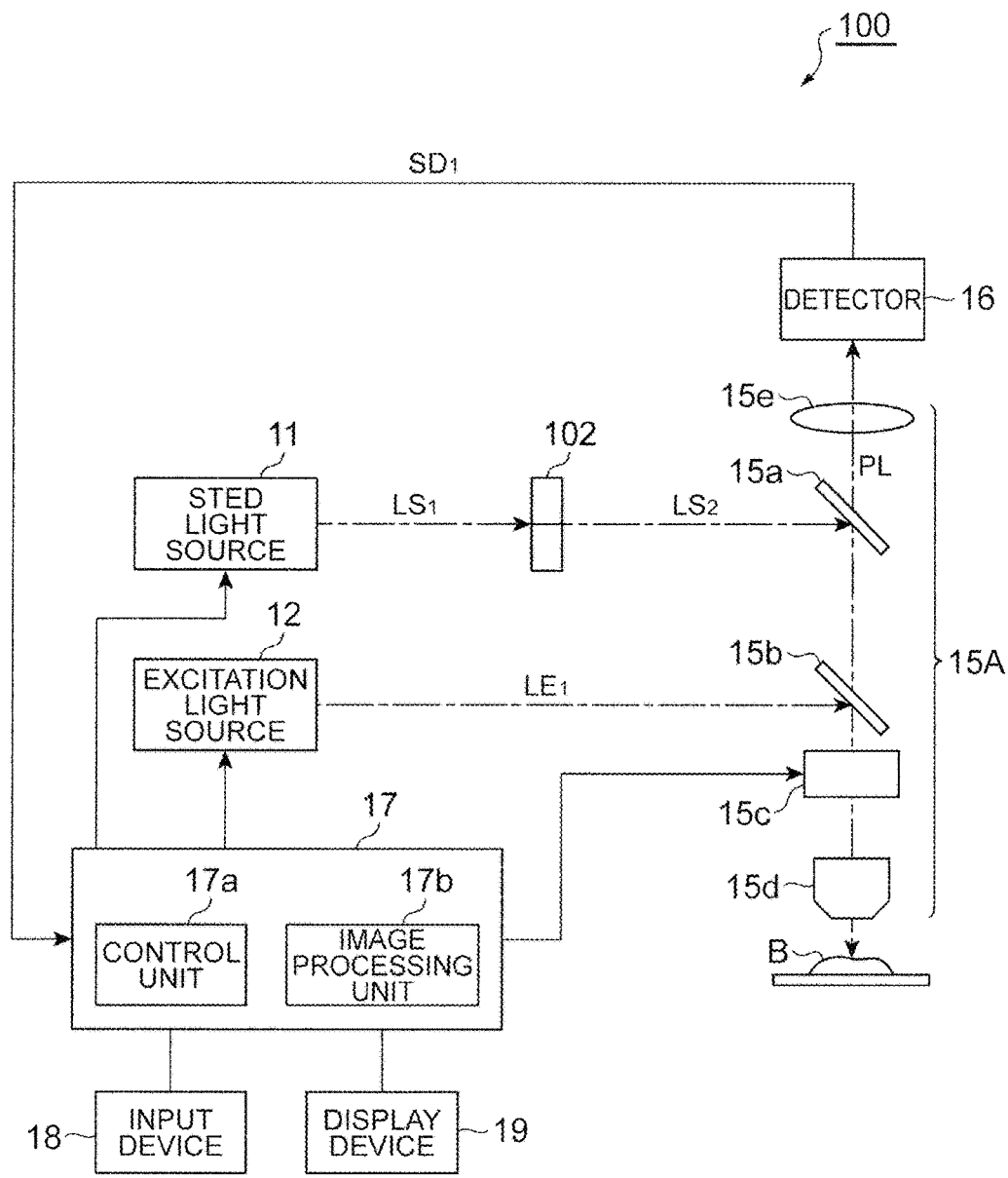
FIG. 9 is a block diagram showing a configuration of an STED microscope apparatus of a comparative example.

Further, FIG. 9 is a block diagram showing a configuration of an STED microscope apparatus 100 of a comparative example. The STED microscope apparatus 100 includes a phase plate 102 for shaping STED light $LS_2$ in an annular shape without including the SLMs 13 and 14. In this configuration, in order to change an inner diameter $D_1$ of the annular shape of the STED light $LS_2$, the phase plate 102 should be substituted with a different phase plate.

On the other hand, in the STED microscope apparatus 1A of the embodiment, the inner diameter $D_1$ of the annular shape of the STED light $LS_2$ after phase modulation can be set or changed by the control unit 17a setting or changing the phase pattern. Accordingly, the inner diameter $D_1$ of the annular shape can be reduced when improvement of the resolution is required, and the inner diameter $D_1$ of the annular shape can be increased when a time required to scan the entire observation object region is decreased. In this way, according to the STED microscope apparatus 1A of the embodiment, user convenience related to the resolution and the required time can be improved.

Further, as in the embodiment, the STED microscope apparatus 1A may include the SLM 14 for shaping the excitation light $LE_2$ in a circular shape by phase modulation, and the control unit 17a may control the excitation light shaping phase pattern presented in the SLM 14. Accordingly, a shape of the excitation light $LE_2$ can be arbitrarily and easily controlled.

Further, as shown in FIG. 3 and FIG. 4, the STED light shaping phase pattern may include any one of the patterns $P_{11}$ to $P_{14}$ in which an increase of the phase from 0 (rad) to $2\pi$ (rad) is repeated n times spirally around a certain point A, and the control unit 17a may control the inner diameter $D_1$ of the annular shape by setting or changing the integer n. The inner diameter $D_1$ of the annular shape of the STED light $LS_2$ after phase modulation can be appropriately controlled, for example, by the above STED light shaping phase pattern.

Further, as in the embodiment, the control unit 17a may have the storage unit 17c for storing a plurality of patterns corresponding to the plurality of inner diameters $D_1$ of the annular shape of the STED light $LS_2$, and the selected pattern may be included in the STED light shaping phase pattern. Accordingly, the user can easily set or change the STED light shaping phase pattern according to the desired resolution or the required time.

Further, as in the embodiment, the detector 16 may detect the light via the optical scanner 15c. Accordingly, a confocal image can be acquired without using a confocal pinhole as a common confocal microscope apparatus.

First Modification Example

Figure 10:
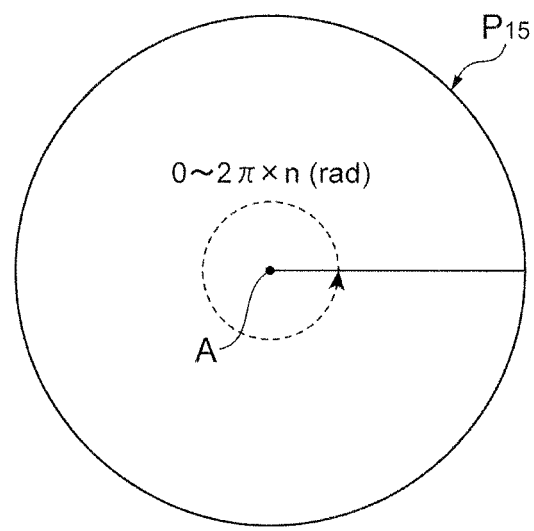
FIG. 10 is a view conceptually showing a pattern for shaping STED light in an annular shape included in an STED light shaping phase pattern presented in the SLM.

FIG. 10 is a view conceptually showing a pattern $P_{15}$ for shaping STED light $LS_2$ in an annular shape, which is included in the STED light shaping phase pattern presented in the SLM 13. In the embodiment, the control unit 17a may superimpose the pattern $P_{15}$ shown in FIG. 10 on the STED light shaping phase pattern presented in the SLM 13, instead of the patterns $P_{11}$ to $P_{14}$ shown in FIG. 3.

As shown in FIG. 10, the pattern $P_{15}$ is a pattern in which a phase increases from 0 (rad) to $2\pi \times n$ (rad) (n is an integer of 1 or more) spirally around a certain point A. For example, in the case of n=2, while the pattern $P_{15}$ is a pattern in which the phase increases from 0 (rad) to $4\pi$ (rad) spirally around the point A, the inner diameter $D_1$ of the annular shape realized by such a pattern is equal to the inner diameter $D_1$ of the annular shape realized by the pattern (see (b) in FIG. 3) in which an increase of the pattern from 0 (rad) to $2\pi$ (rad) spirally is repeated two times. Further, the pattern $P_{15}$ is a phase pattern of a so-called Laguerre-Gaussian (LG) beam. Such a pattern $P_{15}$ can also be expressed using Laguerre polynomials.

As in the modification example, the STED light shaping phase pattern may include the pattern $P_{15}$ in which the phase increases from 0 (rad) to $2\pi \times n$ (rad) spirally around the certain point A, and the control unit 17a may control the inner diameter $D_1$ of the annular shape by setting or changing the integer n. The inner diameter $D_1$ of the annular shape of the STED light $LS_2$ after phase modulation can be appropriately controlled, for example, by the above STED light shaping phase pattern. Further, when the phase modulation width of the SLM 13 is 0 to $2\pi$ (rad), as the patterns $P_{11}$ to $P_{14}$ shown in FIG. 3, a pattern in which an increase of the phase from 0 (rad) to $2\pi$ (rad) spirally is repeated n times (i.e., turns at the phase of $2\pi$) may be used.

Figure 11:
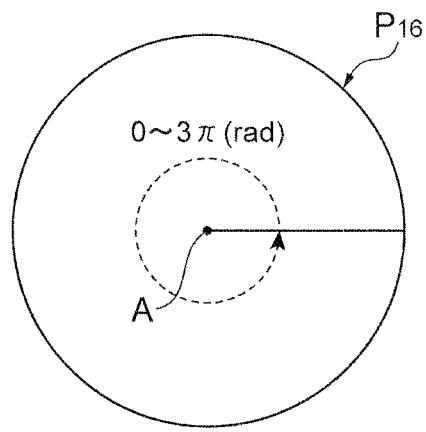
FIG. 11 includes (a), (b) views conceptually showing patterns for shaping STED light in an annular shape included in an STED light shaping phase pattern presented in the SLM, and (c) a view showing a pattern of a comparative example.
Figure 11:
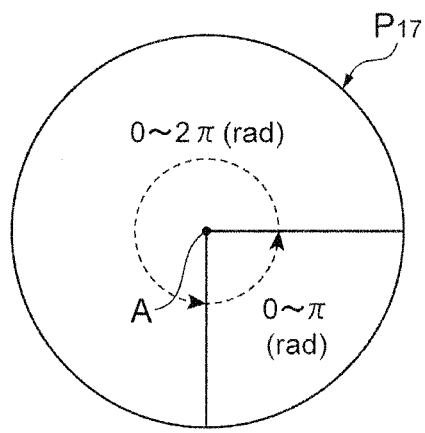
Figure 11:
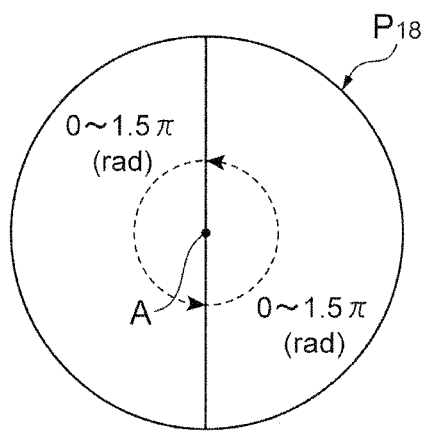

Second Modification Example (a) in FIG. 11 is a view conceptually showing a pattern $P_{16}$ for shaping STED light $LS_2$ in an annular shape, which is included in the STED light shaping phase pattern presented in the SLM 13. In the embodiment, the control unit 17a may superimpose the pattern $P_{16}$ shown in (a) in FIG. 11 on the STED light shaping phase pattern presented in the SLM 13, instead of the patterns $P_{11}$ to $P_{14}$ shown in FIG. 3.

As shown in (a) in FIG. 11, the pattern $P_{16}$ is a pattern in which a phase increases from 0 (rad) to m (rad) (m is a real number of $2\pi$ or more) spirally around a certain point A. For example, in the case of m=$3\pi$, the pattern $P_{16}$ is a pattern in which a phase increases from 0 (rad) to $3\pi$ (rad) spirally around the point A. When the STED light shaping phase pattern includes the pattern $P_{16}$ and the control unit 17a sets or changes the real number m, the inner diameter $D_1$ of the annular shape can also be appropriately controlled. In the modification example, the control unit 17a calculates the real number m that can realize the inner diameter D according to the desired inner diameter $D_1$ input from the input device 18, and superimposes the pattern based on the real number m on the STED light shaping phase pattern.

Further, as shown in (b) in FIG. 11, the pattern of the modification example may be a pattern $P_{17}$ in which a phase increases from 0 (rad) to $2\pi$ (rad) spirally, turns at $2\pi$ (rad), and increases from 0 (rad) to $\pi$ (rad) again. The inner diameter $D_1$ of the annular shape realized by the above-described pattern $P_{17}$ is equal to the inner diameter $D_1$ of the annular shape realized by the pattern $P_{16}$ in which the phase increases from 0 (rad) to $3\pi$ (rad) spirally. However, as shown in (c) in FIG. 11, with a pattern $P_{18}$ in which a phase increases from 0 (rad) to $1.5\pi$ (rad) spirally, turns at $1.5\pi$ (rad), and increases from 0 (rad) to $1.5\pi$ (rad) again, the STED light $LS_2$ cannot be shaped in an annular shape.

Figure 12:
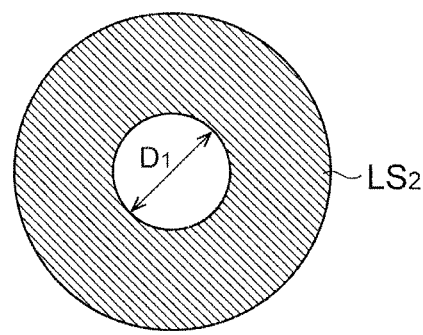
FIG. 12 includes (a)-(c) views schematically showing annular shapes of STED light when $m=2\pi$, $2\pi<m<4\pi$, and $m=4\pi$.
Figure 12:
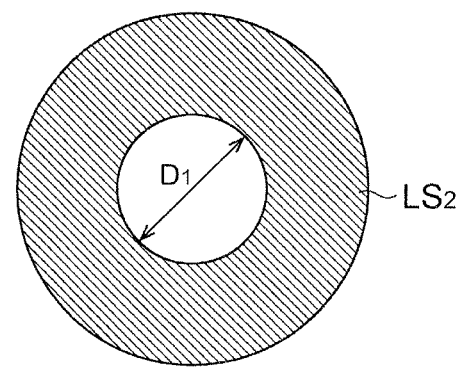
Figure 12:
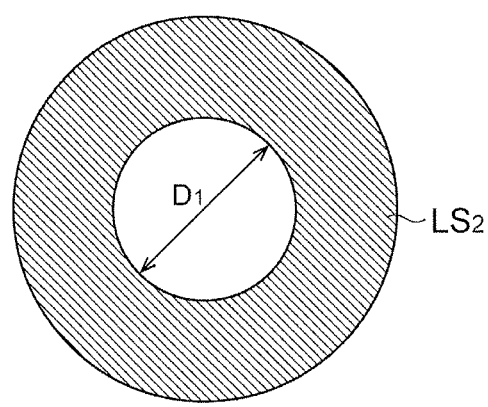

(a) in FIG. 12 to (c) in FIG. 12 are views schematically showing the annular shapes of the STED light $LS_2$ in the case of m=$2\pi$, $2\pi$<m<$4\pi$, and m=$4\pi$, respectively. As shown in FIG. 12, the inner diameter $D_1$ of the annular shape decreases as the value of m decreases, and the inner diameter $D_1$ of the annular shape increases as the value of m increases. Accordingly, the inner diameter $D_1$ of the annular shape can be appropriately controlled by the control unit 17a setting the real number m.

Third Modification Example

Figure 13:
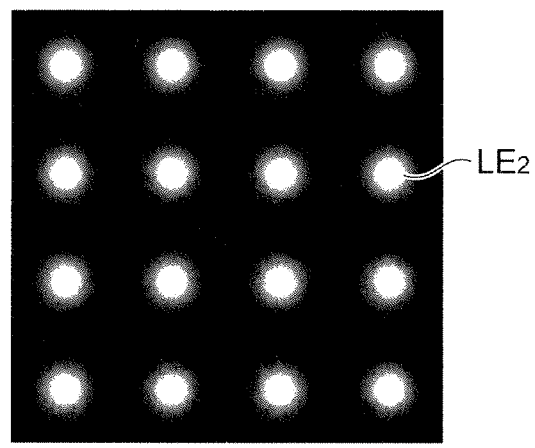
FIG. 13 includes (a) a view showing a plurality of excitation light components generated by dividing excitation light, (b) a view showing a plurality of STED light components generated by dividing STED light, and (c) a view showing a plurality of fluorescence components.
Figure 13:
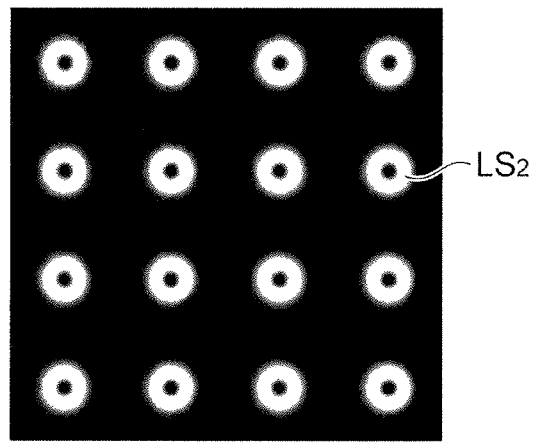
Figure 13:
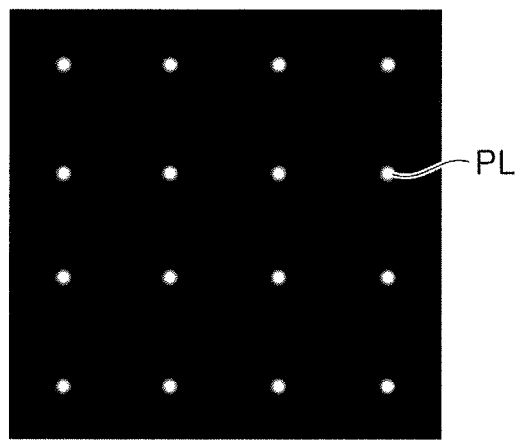

In the embodiment, the control unit 17a may further superimpose a pattern for dividing excitation light $LE_1$ and simultaneously irradiating a plurality of regions with the excitation light components $LE_2$ after division on the excitation light shaping phase pattern. (a) in FIG. 13 is a view showing a plurality of excitation light components $LE_2$ generated by dividing the excitation light $LE_1$. In this case, the control unit 17a may further superimpose a pattern for dividing the STED light $LS_1$ into a plurality of components and simultaneously irradiating a plurality of regions of the observation object B with the STED light components $LS_2$ after division on the STED light shaping phase pattern.

(b) in FIG. 13 is a view showing the plurality of STED light components $LS_2$ generated by dividing the STED light $LS_1$. When irradiation with the STED light $LS_2$ of (b) in FIG. 13 is performed immediately after irradiation with the excitation light $LE_2$ of (a) in FIG. 13, as shown in (c) in FIG. 13, the fluorescence components PL are simultaneously generated from the plurality of regions of the observation object B. Here, in (a) in FIG. 13 to (c) in FIG. 13, light intensity is shown by the density of color, where the density is decreased as the light intensity increases and the density is increased as the light intensity decreases.

Figure 14:
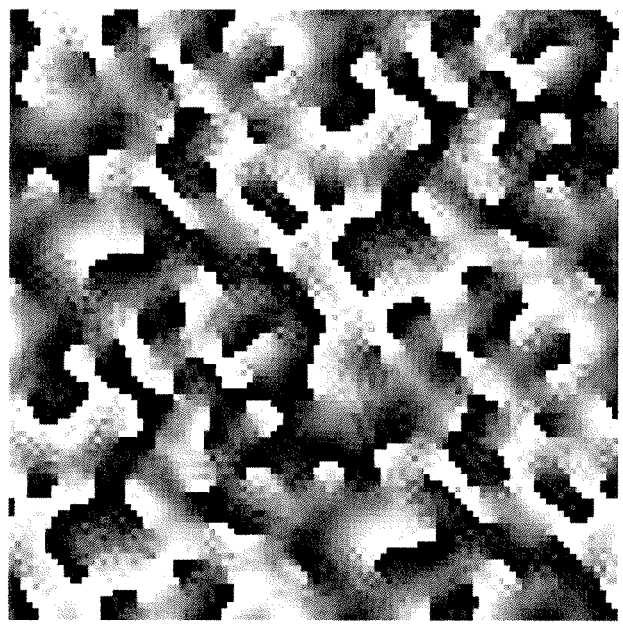
FIG. 14 is a view showing an example of a pattern for generating a plurality of STED light components by dividing STED light.

FIG. 14 is a view showing an example of a pattern for generating the plurality of STED light components $LS_2$ by dividing the STED light $LS_1$. In FIG. 14, phase values of pixels are expressed by the density of color, where the phase value approaches 0 (rad) as the density of color is decreased and the phase value approaches $2\pi$ (rad) as the density of color is increased. In the modification example, for example, as the pattern shown in FIG. 14 is superimposed on the pattern for shaping in an annular shape (for example, the patterns $P_{11}$ to $P_{14}$ shown in FIG. 3), the plurality of STED light components $LS_2$ of the annular shape are generated. Further, the pattern for generating the plurality of excitation light components $LE_2$ by dividing the excitation light $LE_1$ is also superimposed on the pattern for shaping the excitation light $LE_2$ in a circular shape. Further, the pattern shown in FIG. 14 is designed based on the wavelength of the STED light $LS_1$.

According to the modification example, the plurality of regions of the observation object B can be simultaneously observed. Accordingly, since the scan time by the optical scanner 15c is short, a time required for observation can be further reduced.

Fourth Modification Example

Figure 15:
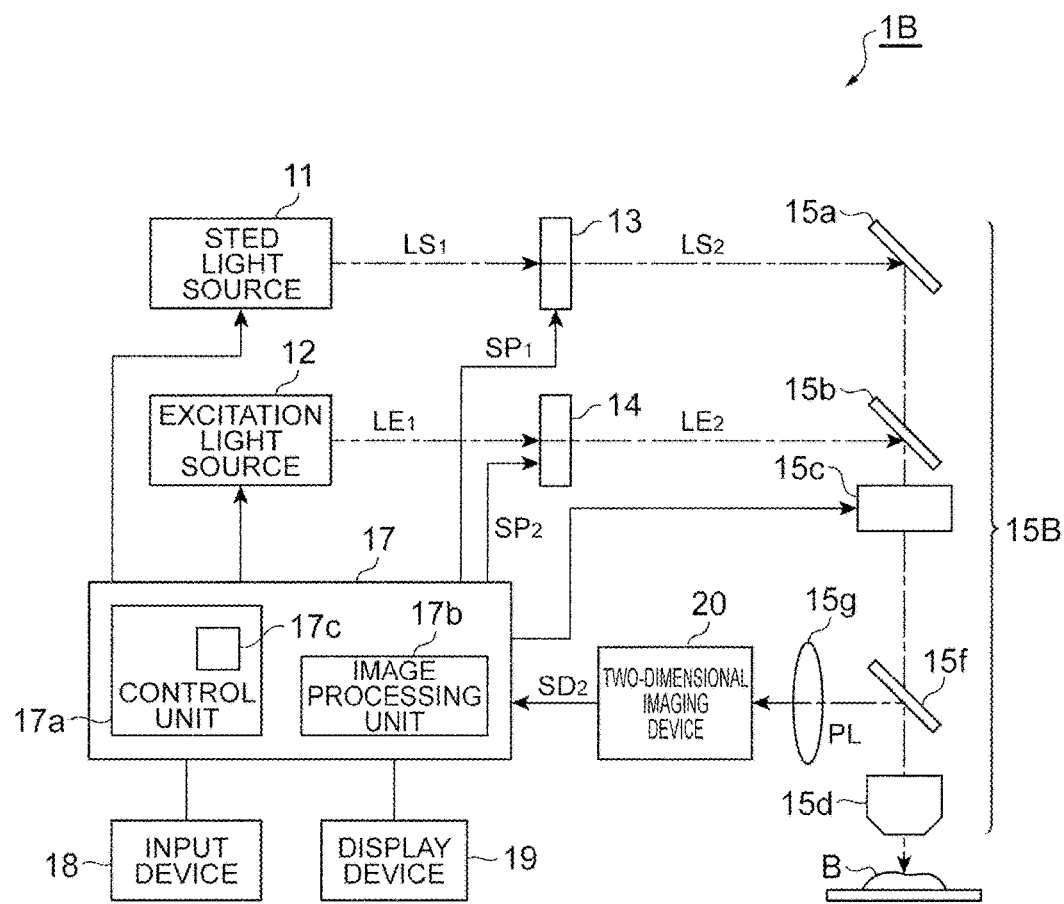
FIG. 15 is a block diagram showing a configuration of an STED microscope apparatus of a fourth modification example.

FIG. 15 is a block diagram showing a configuration of an STED microscope apparatus 1B as a fourth modification example of the embodiment. A point of difference between the STED microscope apparatus 1B of the modification example and the STED microscope apparatus 1A of the embodiment is an imaging method of the fluorescence PL. That is, the STED microscope apparatus 1B of the modification example includes an optical system 15B and a two-dimensional imaging device 20, instead of the optical system 15A and the detector 16 of the embodiment. Further, the other configurations in the STED microscope apparatus 1B are the same as those of the embodiment.

The optical system 15B is provided for irradiating the observation object region of the observation object B with the excitation light $LE_2$ and the STED light $LS_2$. The optical system 15B has the objective lens 15d optically coupled at least to the SLM 13 and the excitation light source 12. Further, in the STED microscope apparatus 1B, the optical system 15B has the dichroic mirrors 15a and 15b, the optical scanner 15c, the objective lens 15d, a dichroic mirror 15f, and an imaging optical system 15g. Further, the configurations of the dichroic mirrors 15a and 15b, the optical scanner 15c, and the objective lens 15d are the same as those of the embodiment.

The dichroic mirror 15f reflects light of a wavelength band including a wavelength of the fluorescence PL generated in the observation object B, and transmits light of a wavelength band including a wavelength of the STED light $LS_2$ and a wavelength of the excitation light $LE_2$. Further, in the modification example, the wavelength of the STED light $LS_2$ is set to a wavelength between the wavelength of the fluorescence PL and the wavelength of the excitation light $LE_2$. The dichroic mirror 15f is disposed on an optical axis that couples the objective lens 15d and the optical scanner 15c. The dichroic mirror 15f receives the fluorescence PL from the observation object B and reflects the fluorescence PL toward the two-dimensional imaging device 20. The imaging optical system 15g is disposed between the dichroic mirror 15f and the two-dimensional imaging device 20, receives the fluorescence PL reflected by the dichroic mirror 15f, and images the fluorescence PL on a detection surface of the two-dimensional imaging device 20.

The two-dimensional imaging device 20 detects the light intensity of the fluorescence PL imaged by the imaging optical system 15g. The two-dimensional imaging device 20 is not optically coupled to the optical scanner 15c, and detects the fluorescence PL generated in the observation object B without interposition of the optical scanner 15c. For example, an area image sensor such as a CCD image sensor or a CMOS image sensor is appropriately used as the two-dimensional imaging device 20. The two-dimensional imaging device 20 provides an optical image signal $SD_2$ showing an optical image of the fluorescence PL to the arithmetic control device 17. The image processing unit 17b of the arithmetic control device 17 generates a fluorescence image based on the optical image of the fluorescence PL captured by the two-dimensional imaging device 20. The fluorescence image generated by the image processing unit 17b is displayed on the display device 19.

Figure 16:
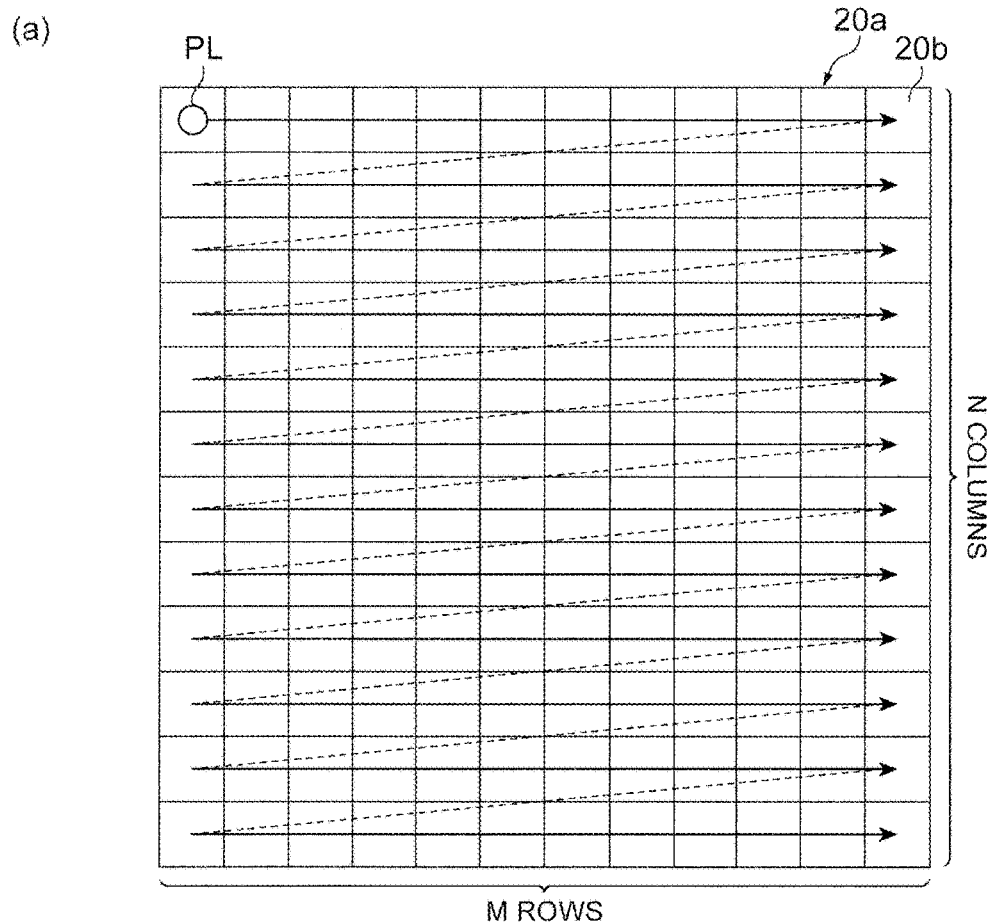
FIG. 16 includes (a) a view schematically showing a state in which an imaging point of fluorescence is scanned on a light receiving surface of a two-dimensional imaging device of the fourth modification example, and (b) a graph showing irradiation timings of excitation light and STED light.
Figure 16:
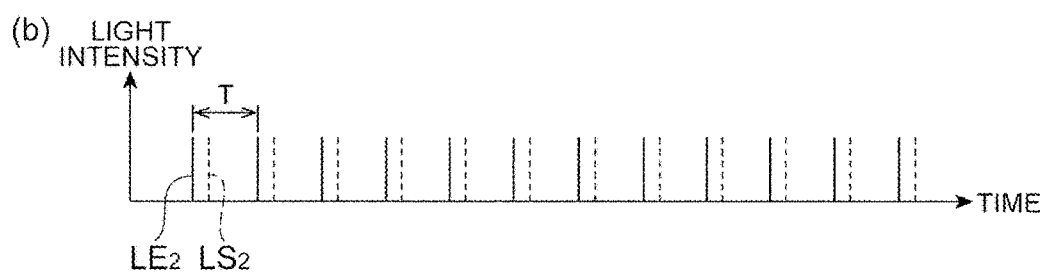

(a) in FIG. 16 is a view schematically showing a state in which an imaging point of the fluorescence PL is scanned on a light receiving surface 20a of the two-dimensional imaging device 20 of the modification example. In (a) in FIG. 16, a scanning direction of the fluorescence PL is represented by a solid arrow. The light receiving surface 20a has a plurality of pixels 20b arrayed two-dimensionally in M rows and N columns (M and N are integers of 2 or more). The optical scanner 15c controls irradiation positions of the excitation light $LE_2$ and the STED light $LS_2$ such that the pixels 20b are scanned with the fluorescence PL in a row direction, wherein scan of one row is completed, and then scan of the next row is performed. Further, an exposure time of the two-dimensional imaging device 20 is set to a time from a scan start to a scan end of the fluorescence PL.

Further, (b) in FIG. 16 is a graph showing irradiation timings of the excitation light $LE_2$ and the STED light $LS_2$, and a horizontal axis corresponds to the scan time of the one row shown in (a) in FIG. 16. In the modification example, in order to improve the resolution, the one pixel 20b is preferably prevented from receiving the fluorescence PL a plurality of times. Accordingly, a pulse time interval T of the excitation light $LE_2$ and the STED light $LS_2$ is preferably set according to a width of the pixel 20b in the scanning direction, a scanning speed of the optical scanner 15c, and imaging magnifications of the objective lens 15d and the imaging optical system 15g.

Specifically, as shown in (b) in FIG. 16, first, when the optical axis of the fluorescence PL is positioned at the first pixel 20b of the row, irradiations with the excitation light $LE_2$ and the STED light $LS_2$ are continuously performed, and the fluorescence PL generated at this time enters the first pixel 20b. Next, after the optical axes of the excitation light $LE_2$ and the STED light $LS_2$ are moved by the optical scanner 15c such that the optical axis of the fluorescence PL is positioned at the next pixel 20b of the row, irradiations with the excitation light $LE_2$ and the STED light $LS_2$ are continuously performed, and the fluorescence PL generated at this time enters the next pixel 20b. By repeatedly performing the above operation throughout the plurality of pixels 20b of the row, the fluorescence image of one row is obtained. Then, by repeating the above operation throughout the plurality of rows, a fluorescence image of one frame is obtained.

Fifth Modification Example

Figure 17:
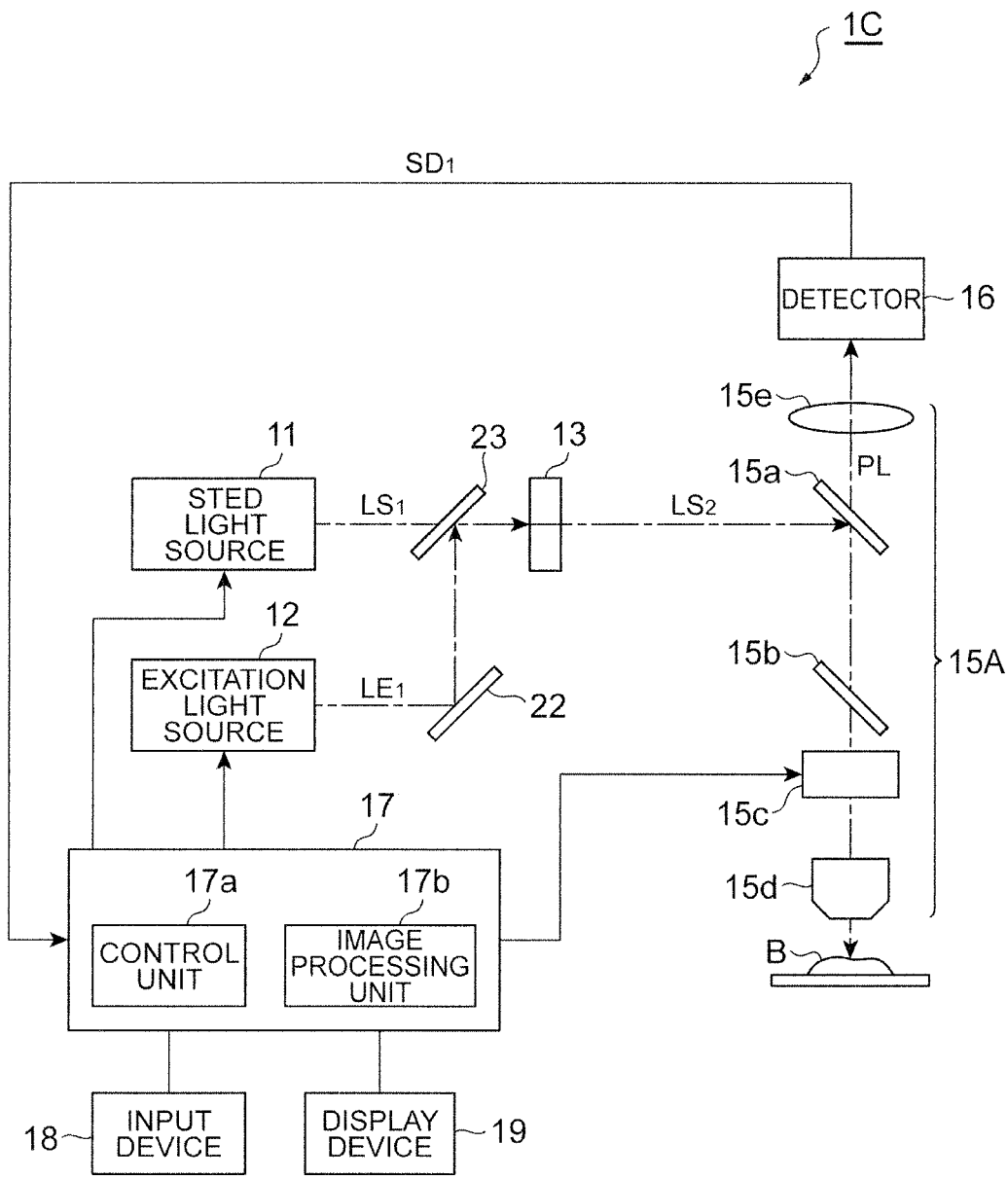
FIG. 17 is a block diagram showing a configuration of an STED microscope apparatus of a fifth modification example.
Figure 18:
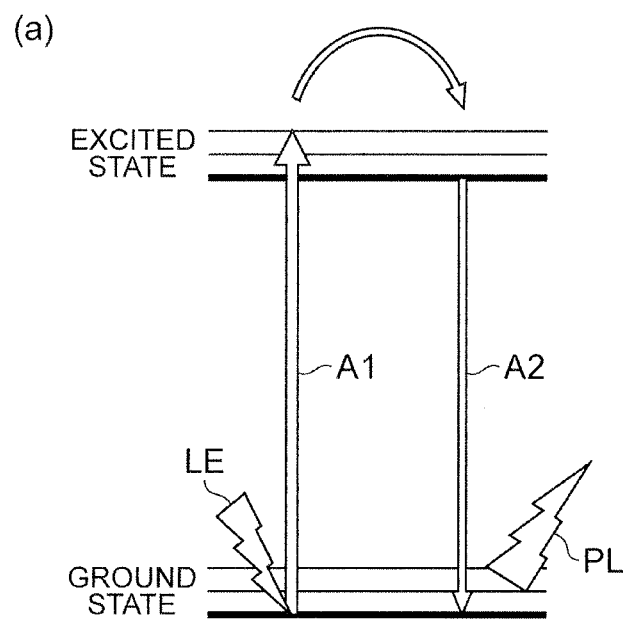
FIG. 18 includes (a), (b) views showing a generation principle of fluorescence.
Figure 18:
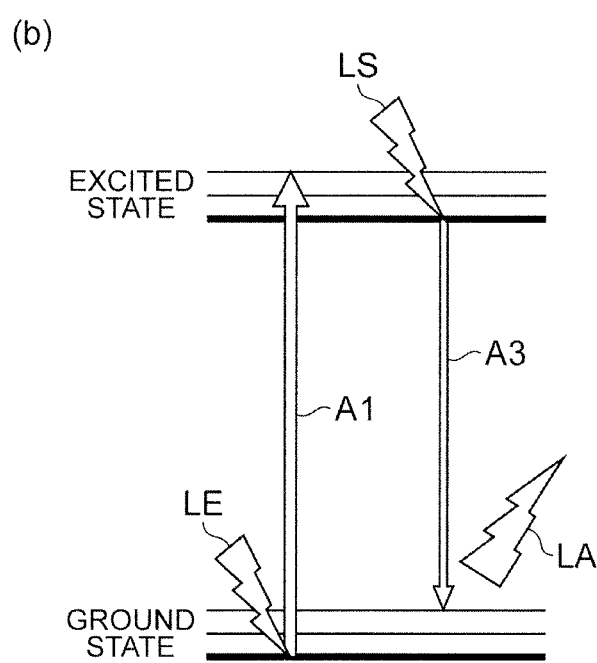

FIG. 17 is a block diagram showing a configuration of an STED microscope apparatus 1C of a fifth modification example of the embodiment. A point of difference between the STED microscope apparatus 1C of the modification example and the STED microscope apparatus 1A of the embodiment is that the SLM 14 for receiving the excitation light $LE_1$ from the excitation light source 12 and outputting the excitation light $LE_2$ after modulation is not used. That is, the STED microscope apparatus 1C of the modification example includes a mirror 22 and a dichroic mirror 23, and thus causes the optical axis of the excitation light $LE_1$ from the excitation light source 12 and the optical axis of the STED light $LS_1$ from the STED light source 11 to coincide with each other and receive both of the STED light $LS_1$ and the excitation light $LE_1$ in the SLM 13. Accordingly, the SLM 13 is optically coupled to the STED light source 11 and the excitation light source 12. Further, the other configurations in the STED microscope apparatus 1C are the same as those of the embodiment.

The excitation light $LE_1$ from the excitation light source 12 is reflected by the mirror 22 and input into the dichroic mirror 23. Since the dichroic mirror 23 transmits the wavelength of the STED light $LS_1$ and reflects the excitation light $LE_1$, it is possible for the optical axis of the excitation light $LE_1$ from the excitation light source 12 and the optical axis of the STED light $LS_1$ from the STED light source 11 to coincide with each other, and the SLM 13 receives the excitation light $LE_1$ and the STED light $LS_1$.

Here, when the SLM 13 is a spatial light modulator for modulating only specific polarization light, such as an LCOS-SLM or the like, by setting the polarization of the STED light $LS_1$ as the specific polarization and the polarization of the excitation light $LE_1$ as polarization perpendicular to the specific polarization, only the STED light $LS_1$ can be modulated. Specifically, when the SLM 13 is the LCOS-SLM, the LCOS-SLM enables phase modulation only for a polarization component (for example, a horizontal polarization component) of the same direction as an orientation direction of a liquid crystal. For this reason, when the STED light $LS_1$ to be phase-modulated to become an annular shape is horizontally polarized and the excitation light $LE_1$ with no necessity of phase modulation is vertically polarized to previously coaxially multiplex these light components, and the light is input into the SLM 13, the STED light $LS_1$ is phase-modulated and output as the STED light $LS_2$. Meanwhile, the excitation light $LE_1$ is output as the excitation light $LE_1$ without modulation. Further, in the STED microscope apparatus 1C, instead of the optical system 15A and the detector 16, the optical system 15B and the two-dimensional imaging device 20 in the STED microscope apparatus 1B may be used.

According to the above-described configuration of the STED microscope apparatus 1C of the modification example, between the STED light source 11, the excitation light source 12, and the SLM 13, the light can be guided using, for example, a polarization fiber in which polarization is maintained, and the STED light source 11 and the excitation light source 12 can be physically separated from the optical system 15A. Accordingly, an influence of vibrations and heat generated in the STED light source 11 and the excitation light source 12 on the optical system 15A is suppressed, downsizing and stabilization of the optical system 15A is achieved, and further, change of the STED light source 11 or the excitation light source 12 becomes easy.

The STED microscope apparatus according to the present invention is not limited to the above-described embodiment, configuration examples, and modification examples, but various modifications may be made.

The stimulated emission depletion (STED) microscope apparatus according to the embodiment includes a stimulated emission depletion light source (an STED light source) for generating stimulated emission depletion light (STED light), an excitation light source for generating excitation light, a phase modulation type first spatial light modulator for presenting a first phase pattern for shaping the stimulated emission depletion light in an annular shape by phase modulation, an optical system for irradiating an observation object region with the excitation light and the stimulated emission depletion light after phase modulation, a detector for detecting fluorescence generated from the observation object region, and a control unit for controlling the first phase pattern, and an inner diameter of the annular shape of the stimulated emission depletion light after phase modulation is able to be changed by the control unit changing the first phase pattern.

Furthermore, the stimulated emission depletion (STED) microscope apparatus according to the embodiment includes a stimulated emission depletion light source (an STED light source) outputting stimulated emission depletion light (STED light), an excitation light source outputting excitation light, a phase modulation type first spatial light modulator optically coupled to the stimulated emission depletion light source and presenting a first phase pattern for shaping the stimulated emission depletion light in an annular shape by phase modulation, an optical system optically coupled to the excitation light source and the first spatial light modulator and irradiating an observation object region with the excitation light and the stimulated emission depletion light after phase modulation, a detector optically coupled to the optical system and detecting fluorescence generated from the observation object region, and a control unit electrically coupled to the first spatial light modulator and controlling the first phase pattern, and the control unit sets the first phase pattern for controlling an inner diameter of an annular shape of the stimulated emission depletion light after phase modulation.

Further, the stimulated emission depletion (STED) microscopy method according to the embodiment includes a step of outputting stimulated emission depletion light (STED light) by a stimulated emission depletion light source (an STED light source) (a stimulated emission depletion light output step, an STED light output step), a step of outputting excitation light by an excitation light source (an excitation light output step), a step of phase-modulating the stimulated emission depletion light by a phase modulation type first spatial light modulator optically coupled to the stimulated emission depletion light source and presenting a first phase pattern for shaping the stimulated emission depletion light in an annular shape (a modulation step, a first modulation step), a step of irradiating an observation object region with the excitation light and the stimulated emission depletion light after phase modulation by an optical system optically coupled to the excitation light source and the first spatial light modulator (an irradiation step), a step of detecting fluorescence generated from the observation object region by a detector optically coupled to the optical system (a detection step), and a step of setting the first phase pattern for controlling an inner diameter of the annular shape of the stimulated emission depletion light after phase modulation (a setting step).

Further, the STED microscope apparatus may further include a second spatial light modulator optically coupled to the excitation light source and presenting a second phase pattern for shaping the excitation light in a circular shape by phase modulation, and the control unit may further control the second phase pattern. Further, the STED microscopy method may further include a step of phase-modulating the excitation light by a second spatial light modulator optically coupled to the excitation light source and presenting a second phase pattern for shaping the excitation light in a circular shape (a second modulation step). In this case, a shape and a size of the excitation light can be arbitrarily controlled.

Further, the STED microscope apparatus may be configured such that the control unit superimposes a pattern for dividing the STED light to irradiate a plurality of regions on the first phase pattern, and superimposes a pattern for dividing the excitation light to irradiate a plurality of regions on the second phase pattern. Further, in the STED microscopy method, in the first modulation step, a pattern for dividing the STED light to irradiate a plurality of regions may be superimposed on the first phase pattern, and in the second modulation step, a pattern for dividing the excitation light to irradiate a plurality of regions may be superimposed on the second phase pattern. In this case, the plurality of regions can be simultaneously observed, and the required time can be further reduced.

Further, in the STED microscope apparatus and the STED microscopy method, the detector may be a two-dimensional detector.

Further, in this case, the STED microscope apparatus may further include an optical scanner for scanning a light receiving surface of the two-dimensional detector with the fluorescence, and an irradiation time interval of the excitation light and the stimulated emission depletion light may be set such that each of pixels does not receive the fluorescence a plurality of times according to a width of the pixel on the light receiving surface and a scanning speed of the optical scanner in a scanning direction. Further, the STED microscopy method may further include a step of scanning the fluorescence on a light receiving surface of the two-dimensional detector by an optical scanner (a scan step), and an irradiation time interval of the excitation light and the stimulated emission depletion light may be set such that each of pixels does not receive the fluorescence a plurality of times according to a width of the pixel on the light receiving surface and a scanning speed of the optical scanner in a scanning direction. In this case, resolution can be improved.

Further, in the STED microscope apparatus, the first phase pattern may include a pattern in which a phase increases from 0 (rad) to $2\pi \times n$ (rad) (n is an integer of 1 or more) spirally around a certain point, and the control unit may be configured to set the integer n for controlling the inner diameter of the annular shape. Further, in the STED microscopy method, the first phase pattern may include a pattern in which a phase increases from 0 (rad) to $2\pi \times n$ (rad) (n is an integer of 1 or more) spirally around a certain point, and in the setting step, the integer n may be set for controlling the inner diameter of the annular shape. For example, the inner diameter of the annular shape of the STED light after phase modulation can be appropriately controlled by the above-described first phase pattern.

Further, in the STED microscope apparatus, the first phase pattern may include a pattern in which an increase of a phase from 0 (rad) to $2\pi$ (rad) spirally around a certain point is repeated n times (n is an integer of 1 or more), and the control unit may be configured to set the integer n for controlling the inner diameter of the annular shape. Further, in the STED microscopy method, the first phase pattern may include a pattern in which an increase of a phase from 0 (rad) to $2\pi$ (rad) spirally around a certain point is repeated n times (n is an integer of 1 or more), and in the setting step, the integer n may be set for controlling the inner diameter of the annular shape. For example, the inner diameter of the annular shape of the STED light after phase modulation can be appropriately controlled by the above-described first phase pattern.

Further, the STED microscope apparatus may further include a storage unit for storing a plurality of patterns corresponding to a plurality of inner diameters of the annular shape of the stimulated emission depletion light, and the pattern selected from the plurality of patterns may be included in the first phase pattern. Further, in the STED microscopy method, in the setting step, the pattern selected from a plurality of patterns corresponding to a plurality of inner diameters of the annular shape of the stimulated emission depletion light stored in a storage unit may be included in the first phase pattern. In this case, a user can easily set or change the first phase pattern according to a desired resolution or a required time.

Further, the STED microscope apparatus may further include an input unit for inputting a desired value of the inner diameter of the annular shape, the first phase pattern may include a pattern in which a phase increases from 0 (rad) to m (rad) (m is a real number of $2\pi$ or more) spirally around a certain point, and the control unit may be configured to set the real number m based on the desired value of the inner diameter of the annular shape input from the input unit. Further, in the STED microscopy method, the first phase pattern may include a pattern in which a phase increases from 0 (rad) to m (rad) (m is a real number of $2\pi$ or more) spirally around a certain point, and in the setting step, the real number m may be set based on a desired value of the inner diameter of the annular shape input from an input unit. For example, the inner diameter of the annular shape of the STED light after phase modulation can be appropriately controlled by the above-described first phase pattern.

INDUSTRIAL APPLICABILITY

The present invention can be used as the STED microscope apparatus capable of improving user convenience related to the resolution and the required time.

REFERENCE SIGNS LIST

1A—STED microscope apparatus, 1B—STED microscope apparatus, 11—STED light source, 12—excitation light source, 13, 14—SLM, 15A, 15B—optical system, 15a, 15b—dichroic mirror, 15c—optical scanner, 15d—objective lens, 15e—imaging optical system, 15f-dichroic mirror, 15g—imaging optical system, 16—detector, 17—arithmetic control device, 17a—control unit, 17b—image processing unit, 17c—storage unit, 18—input device, 19—display device, 20—two-dimensional imaging device, 20a—light receiving surface, 20b—pixel, B—observation object, $LE_1$, $LE_2$—excitation light, $LS_1$, $LS_2$—STED light, PL—fluorescence.

The invention claimed is:

1. A stimulated emission depletion microscope apparatus comprising:
a stimulated emission depletion light source configured to output stimulated emission depletion light;
an excitation light source configured to output excitation light;
a phase modulation type first spatial light modulator configured to modulate the stimulated emission depletion light based on a first phase pattern for shaping the stimulated emission depletion light in an annular shape;
an optical system comprising at least one of a dichroic mirror, an optical scanner, and an objective lens, the optical system configured to irradiate an observation object region with the excitation light and the modulated stimulated emission depletion light;
a detector configured to detect fluorescence generated from the observation object region; and
controller configured to determine the first phase pattern based on an inner diameter of the annular shape.

2. The stimulated emission depletion microscope apparatus according to claim 1, further comprising a second spatial light modulator configured to modulate the excitation light based on a second phase pattern for shaping the excitation light in a circular shape, wherein
the controller is configured to determine the second phase pattern based on a diameter of the circular shape.

3. The stimulated emission depletion microscope apparatus according to claim 2, wherein the controller is configured to superimpose a pattern for dividing the stimulated emission depletion light to irradiate a plurality of regions on the first phase pattern, and superimpose a pattern for dividing the excitation light to irradiate the plurality of regions on the second phase pattern.

4. The stimulated emission depletion microscope apparatus according to claim 3, wherein the detector comprises a two-dimensional detector.

5. The stimulated emission depletion microscope apparatus according to claim 4, further comprising the optical scanner configured to scan a light receiving surface of the two-dimensional detector with the fluorescence, wherein
an irradiation time interval of the excitation light and the stimulated emission depletion light is set such that each of pixels does not receive the fluorescence a plurality of times according to a width of the pixel on the light receiving surface and a scanning speed of the optical scanner in a scanning direction.

6. The stimulated emission depletion microscope apparatus according to claim 1, wherein the first phase pattern includes a pattern in which a phase increases from 0 (rad) to $2\pi \times n$ (rad) (n is an integer of 1 or more) spirally around a certain point, and
the controller is configured to set the integer n for controlling the inner diameter of the annular shape.

7. The stimulated emission depletion microscope apparatus according to claim 1, wherein the first phase pattern includes a pattern of repeating an increase of a phase from 0 (rad) to $2\pi$ (rad) spirally around a certain point n times (n is an integer of 1 or more), and
the controller is configured to set the integer n for controlling the inner diameter of the annular shape.

8. The stimulated emission depletion microscope apparatus according to claim 1, further comprising a storage unit for storing configured to store a plurality of patterns corresponding to a plurality of inner diameters of the annular shape of the stimulated emission depletion light, wherein the pattern selected from the plurality of patterns is included in the first phase pattern.

9. The stimulated emission depletion microscope apparatus according to claim 1, wherein
the first phase pattern includes a pattern in which a phase increases from 0 (rad) to m (rad) (m is a real number of $2\pi$ or more) spirally around a certain point, and
the controller is configured to input a desired value of the inner diameter of the annular shape and set the real number m based on the desired value of the inner diameter of the annular shape.

10. A stimulated emission depletion microscopy method comprising:
outputting stimulated emission depletion light;
outputting excitation light;
modulating the stimulated emission depletion light based on a first phase pattern for shaping the stimulated emission depletion light in an annular shape by a phase modulation type first spatial light modulator;
irradiating an observation object region with the excitation light and the modulated stimulated emission depletion light by an optical system;
detecting fluorescence generated from the observation object region by a detector; and
determining the first phase pattern based on an inner diameter of the annular shape.

11. The stimulated emission depletion microscopy method according to claim 10, further comprising:
modulating the excitation light based on a second phase pattern for shaping the excitation light in a circular shape by a second spatial light modulator; and
determining the second phase pattern based on a diameter of the circular shape.

* * * * *